US010695192B2

(12) United States Patent
Bishop et al.

(10) Patent No.: US 10,695,192 B2
(45) Date of Patent: Jun. 30, 2020

(54) IMPLANT WITH INTERNAL SUPPORT MEMBERS

(71) Applicant: Institute for Musculoskeletal Science and Education, Ltd., Wayne, PA (US)

(72) Inventors: Sean S. Bishop, Malvern, PA (US); Christopher J. Ryan, Lincoln University, PA (US); Edward J. McShane, III, Collegeville, PA (US); Joseph M. Nyahay, Eagleville, PA (US); Megan A. Stauffer, Wayne, PA (US)

(73) Assignee: Institute for Musculoskeletal Science and Education, Ltd., King of Prussia, PA (US)

( * ) Notice: Subject to any disclaimer, the term of this patent is extended or adjusted under 35 U.S.C. 154(b) by 0 days.

(21) Appl. No.: 15/885,051

(22) Filed: Jan. 31, 2018

(65) Prior Publication Data

US 2019/0231554 A1    Aug. 1, 2019

(51) Int. Cl.
*A61F 2/44* (2006.01)
*A61F 2/30* (2006.01)
*A61F 2/46* (2006.01)

(52) U.S. Cl.
CPC ........ *A61F 2/4465* (2013.01); *A61F 2/30771* (2013.01); *A61F 2/4611* (2013.01); *A61F 2/4455* (2013.01); *A61F 2002/3092* (2013.01); *A61F 2002/3093* (2013.01); *A61F 2002/30128* (2013.01); *A61F 2002/30131* (2013.01); *A61F 2002/30179* (2013.01); *A61F 2002/30289* (2013.01); *A61F 2002/4629* (2013.01)

(58) Field of Classification Search
CPC ... A61F 2/4465; A61F 2/30771; A61F 2/4611
See application file for complete search history.

(56) References Cited

U.S. PATENT DOCUMENTS

| 4,961,740 A | 10/1990 | Ray et al. |
| 5,458,638 A | 10/1995 | Kuslich et al. |

(Continued)

FOREIGN PATENT DOCUMENTS

| WO | 2009051779 A1 | 4/2009 |
| WO | 2010097632 A1 | 9/2010 |

(Continued)

OTHER PUBLICATIONS

International Search Report and Written Opinion dated May 16, 2019, for PCT Application No. PCT/US2019/15938.

*Primary Examiner* — Tessa M Matthews
(74) *Attorney, Agent, or Firm* — Plumsea Law Group, LLC

(57) ABSTRACT

An implant includes a central wall extending from a first side of a peripheral frame portion to a second side of the peripheral frame portion, and a first helical bone contacting member attached at the central wall and disposed within the superior half of the implant. The implant further includes a first support member attached at the central wall at a junction coincident with the first helical bone contacting member and extending to a central region of the implant internal to the first helical bone contacting member. In addition, the implant includes a non-helical bone contacting member extending from a portion of the first support member that is disposed internal to the first helical bone contacting member.

20 Claims, 29 Drawing Sheets

(56) References Cited

U.S. PATENT DOCUMENTS

| | | |
|---|---|---|
| 5,571,192 A | 11/1996 | Schonhoffer |
| 5,607,424 A | 3/1997 | Tropiano |
| 5,609,635 A | 3/1997 | Michelson |
| 5,658,337 A | 8/1997 | Kohrs et al. |
| 5,709,683 A | 1/1998 | Bagby |
| 5,716,416 A | 2/1998 | Lin |
| 5,897,556 A | 4/1999 | Drewry et al. |
| 6,039,762 A | 3/2000 | McKay |
| 6,090,143 A | 7/2000 | Meriwether et al. |
| 6,126,689 A | 10/2000 | Brett |
| 6,149,651 A | 11/2000 | Drewry et al. |
| 6,200,348 B1 | 3/2001 | Biedermann et al. |
| 6,206,924 B1 | 3/2001 | Timm |
| 6,371,987 B1 | 4/2002 | Weiland et al. |
| 6,428,575 B2 | 8/2002 | Koo et al. |
| 6,436,141 B2 | 8/2002 | Castro et al. |
| 6,494,883 B1 | 12/2002 | Ferree |
| 6,500,205 B1 | 12/2002 | Michelson |
| 6,520,996 B1 | 2/2003 | Manasas |
| 6,527,805 B2 | 3/2003 | Studer et al. |
| 6,537,320 B1 | 3/2003 | Michelson |
| 6,582,467 B1 | 6/2003 | Teitelbaum et al. |
| 6,585,770 B1 | 7/2003 | White et al. |
| 6,616,695 B1 | 9/2003 | Crozet et al. |
| 6,709,458 B2 | 3/2004 | Michelson |
| 6,758,849 B1 | 7/2004 | Michelson |
| 6,808,537 B2 | 10/2004 | Michelson |
| 6,846,327 B2 | 1/2005 | Khandkar et al. |
| 6,863,689 B2 | 3/2005 | Ralph et al. |
| 6,923,810 B1 | 8/2005 | Michelson |
| 6,962,606 B2 | 11/2005 | Michelson |
| 6,997,953 B2 | 2/2006 | Chung et al. |
| 7,141,068 B2 | 11/2006 | Ross et al. |
| 7,186,267 B2 | 3/2007 | Aston et al. |
| 7,341,601 B2 | 3/2008 | Eisermann et al. |
| 7,410,501 B2 | 8/2008 | Michelson |
| 7,429,270 B2 | 9/2008 | Baumgartner et al. |
| 7,435,261 B1 | 10/2008 | Castro |
| 7,452,369 B2 | 11/2008 | Barry |
| 7,485,134 B2 | 2/2009 | Simonson |
| 7,527,649 B1 | 5/2009 | Blain |
| 7,537,616 B1 | 5/2009 | Branch et al. |
| 7,621,952 B2 | 11/2009 | Truckai et al. |
| 7,621,953 B2 | 11/2009 | Braddock, Jr. et al. |
| 7,628,814 B2 | 12/2009 | Studer et al. |
| 7,794,500 B2 | 9/2010 | Felix |
| 7,799,056 B2 | 9/2010 | Sankaran |
| 7,803,191 B2 | 9/2010 | Biedermann et al. |
| 7,879,103 B2 | 2/2011 | Gertzman |
| 7,935,149 B2 | 5/2011 | Michelson |
| 8,016,887 B1 | 9/2011 | Castro |
| 8,021,424 B2 | 9/2011 | Beger et al. |
| 8,021,426 B2 | 9/2011 | Segal et al. |
| 8,082,385 B2 | 11/2011 | Schwab |
| 8,092,536 B2 | 1/2012 | Ahrens et al. |
| 8,182,538 B2 | 5/2012 | O'Neil et al. |
| 8,226,718 B2 | 7/2012 | Castro |
| 8,241,363 B2 | 8/2012 | Sommerich et al. |
| 8,246,683 B2 | 8/2012 | Castro |
| 8,298,286 B2 | 10/2012 | Trieu |
| 8,328,848 B2 | 12/2012 | Lowery et al. |
| 8,361,149 B2 | 1/2013 | Castro |
| 8,414,820 B2 | 4/2013 | Bertele et al. |
| 8,430,930 B2 | 4/2013 | Hunt |
| 8,435,300 B2 | 5/2013 | Messerli et al. |
| 8,454,700 B2 | 6/2013 | Lemoine et al. |
| 8,475,533 B1 | 7/2013 | Castro |
| 8,551,173 B2 | 10/2013 | Lechmann et al. |
| 8,556,978 B2 | 10/2013 | Schaller |
| 8,613,769 B2 | 12/2013 | Sears et al. |
| 8,623,090 B2 | 1/2014 | Butler |
| 8,673,006 B2 | 3/2014 | Castro |
| 8,709,042 B2 | 4/2014 | Greenhalgh et al. |
| 8,740,981 B2 | 6/2014 | Tornier et al. |
| 8,771,357 B2 | 7/2014 | Biedermann et al. |
| 8,771,368 B2 | 7/2014 | McKay |
| 8,795,362 B2 | 8/2014 | Anderson et al. |
| 8,801,787 B2 | 8/2014 | Schaller |
| 8,808,376 B2 | 8/2014 | Schaller |
| 8,808,725 B2 | 8/2014 | Altschuler et al. |
| 8,932,356 B2 | 1/2015 | Kraus |
| 8,940,052 B2 | 1/2015 | Lechmann et al. |
| 8,951,300 B2 | 2/2015 | Parrish |
| 8,986,383 B2 | 3/2015 | Castro |
| 9,039,766 B1 | 5/2015 | Fonte |
| 9,173,746 B2 | 11/2015 | Lowery et al. |
| 9,186,252 B2 | 11/2015 | Leibinger |
| 9,186,257 B2 | 11/2015 | Geisler et al. |
| 9,247,970 B2 | 2/2016 | Teisen |
| 9,271,845 B2 | 3/2016 | Hunt et al. |
| 9,295,562 B2 | 3/2016 | Lechmann et al. |
| 9,402,733 B1 | 8/2016 | To et al. |
| 9,408,651 B2 | 8/2016 | Sennett et al. |
| 9,421,108 B2 | 8/2016 | Hunt |
| 2001/0014826 A1 | 8/2001 | Biedermann et al. |
| 2001/0032018 A1 | 10/2001 | Castro et al. |
| 2002/0052656 A1 | 5/2002 | Michelson |
| 2003/0078660 A1 | 4/2003 | Clifford et al. |
| 2003/0083746 A1 | 5/2003 | Kuslich |
| 2004/0193270 A1 | 9/2004 | DiMauro et al. |
| 2004/0210312 A1 | 10/2004 | Neumann |
| 2004/0225361 A1 | 11/2004 | Glenn et al. |
| 2005/0177238 A1 | 8/2005 | Khandkar et al. |
| 2005/0222681 A1 | 10/2005 | Richley et al. |
| 2005/0278027 A1 | 12/2005 | Hyde, Jr. |
| 2006/0041262 A1 | 2/2006 | Calvert et al. |
| 2006/0052872 A1 | 3/2006 | Studer |
| 2006/0100706 A1 | 5/2006 | Shadduck et al. |
| 2006/0147332 A1 | 7/2006 | Jones et al. |
| 2006/0293753 A1 | 12/2006 | Thramann |
| 2007/0027544 A1 | 2/2007 | McCord et al. |
| 2007/0050032 A1 | 3/2007 | Gittings et al. |
| 2007/0179610 A1 | 8/2007 | Biedermann et al. |
| 2007/0198090 A1 | 8/2007 | Abdou |
| 2007/0260324 A1 | 11/2007 | Joshi et al. |
| 2008/0077244 A1 | 3/2008 | Robinson |
| 2008/0306595 A1 | 12/2008 | McLeod et al. |
| 2008/0312742 A1 | 12/2008 | Abernathie |
| 2009/0036985 A1 | 2/2009 | Whiting |
| 2009/0048878 A1 | 2/2009 | Saal et al. |
| 2009/0112321 A1 | 4/2009 | Kitchen |
| 2009/0149958 A1 | 6/2009 | Prewett et al. |
| 2009/0248162 A1 | 10/2009 | Peckham |
| 2010/0286778 A1 | 11/2010 | Eisermann et al. |
| 2011/0015741 A1 | 1/2011 | Melkent et al. |
| 2011/0066192 A1 | 3/2011 | Frasier et al. |
| 2011/0166660 A1 | 7/2011 | Laurence |
| 2011/0190895 A1 | 8/2011 | Segal et al. |
| 2011/0245926 A1 | 10/2011 | Kitchen |
| 2011/0270401 A1 | 11/2011 | McKay |
| 2011/0301709 A1 | 12/2011 | Kraus et al. |
| 2011/0313532 A1 | 12/2011 | Hunt |
| 2012/0191188 A1 | 7/2012 | Huang |
| 2012/0191189 A1 | 7/2012 | Huang |
| 2012/0296431 A1 | 11/2012 | Kim et al. |
| 2013/0030529 A1 | 1/2013 | Hunt |
| 2013/0116793 A1 | 5/2013 | Kloss |
| 2013/0123935 A1 | 5/2013 | Hunt et al. |
| 2013/0158672 A1 | 6/2013 | Hunt |
| 2013/0184826 A1 | 7/2013 | Thaiyananthan |
| 2013/0190880 A1 | 7/2013 | Schaller |
| 2013/0218282 A1 | 8/2013 | Hunt |
| 2013/0218288 A1 | 8/2013 | Fonte et al. |
| 2013/0304211 A1 | 11/2013 | Trautwein et al. |
| 2013/0345812 A1 | 12/2013 | Errico et al. |
| 2014/0058513 A1 | 2/2014 | Gahman et al. |
| 2014/0121770 A1 | 5/2014 | Hunt |
| 2014/0121776 A1* | 5/2014 | Hunt ............... A61F 2/4455 623/17.16 |
| 2014/0142707 A1 | 5/2014 | Compton et al. |
| 2014/0195005 A1 | 7/2014 | McKay |
| 2014/0243980 A1 | 8/2014 | Sack et al. |
| 2014/0277457 A1 | 9/2014 | Yeung et al. |
| 2014/0277464 A1 | 9/2014 | Richter et al. |

(56) References Cited

U.S. PATENT DOCUMENTS

| | | |
|---|---|---|
| 2014/0277569 A1 | 9/2014 | Lange |
| 2014/0288549 A1 | 9/2014 | Hunt |
| 2014/0288649 A1 | 9/2014 | Hunt |
| 2014/0288650 A1 | 9/2014 | Hunt |
| 2014/0303745 A1 | 10/2014 | Anderson et al. |
| 2014/0309743 A1 | 10/2014 | Falahee |
| 2014/0358246 A1 | 12/2014 | Levy et al. |
| 2015/0127106 A1 | 5/2015 | Partee et al. |
| 2015/0282933 A1 | 10/2015 | Hunt |
| 2015/0282945 A1 | 10/2015 | Hunt |
| 2015/0282946 A1 | 10/2015 | Hunt |
| 2016/0045230 A1 | 2/2016 | Lowery et al. |
| 2016/0081809 A1 | 3/2016 | Schneider et al. |
| 2016/0193057 A1 | 7/2016 | Rhode |
| 2016/0206439 A1 | 7/2016 | To et al. |
| 2016/0206440 A1 | 7/2016 | DeRidder et al. |
| 2016/0324656 A1 | 11/2016 | Morris et al. |
| 2017/0042697 A1 | 2/2017 | McShane, III et al. |
| 2017/0156879 A1 | 6/2017 | Janowski |
| 2017/0258606 A1* | 9/2017 | Afzal .................... A61F 2/4465 |
| 2018/0011062 A1 | 1/2018 | Kojima et al. |
| 2018/0110626 A1* | 4/2018 | McShane, III .......... A61F 2/446 |
| 2018/0256351 A1* | 9/2018 | Bishop .................... A61F 2/442 |
| 2018/0256352 A1* | 9/2018 | Nyahay .................. A61F 2/447 |
| 2018/0256361 A1* | 9/2018 | Bishop .................. A61F 2/4455 |
| 2019/0038428 A1* | 2/2019 | Stauffer ................ A61F 2/4455 |

FOREIGN PATENT DOCUMENTS

| | | |
|---|---|---|
| WO | 2011159587 A1 | 12/2011 |
| WO | 2013019543 A2 | 2/2013 |

* cited by examiner

IMPLANT WITH INTERNAL SUPPORT MEMBERS

BACKGROUND

The embodiments are generally directed to implants for supporting bone growth in a patient.

A variety of different implants are used in the body. Implants used in the body to stabilize an area and promote bone ingrowth provide both stability (i.e. minimal deformation under pressure over time) and space for bone ingrowth.

Spinal fusion, also known as spondylodesis or spondylosyndesis, is a surgical treatment method used for the treatment of various morbidities such as degenerative disc disease, spondylolisthesis (slippage of a vertebra), spinal stenosis, scoliosis, fracture, infection or tumor. The aim of the spinal fusion procedure is to reduce instability and thus pain.

In preparation for the spinal fusion, most of the intervertebral disc is removed. An implant, the spinal fusion cage, may be placed between the vertebra to maintain spine alignment and disc height. The fusion, i.e. bone bridge, occurs between the endplates of the vertebrae.

SUMMARY

In one aspect, the present disclosure is directed to an implant includes a body defining a transverse plane dividing the implant into a superior half and an inferior half, the implant having an anterior side and a posterior side. The implant may also include a peripheral frame portion defining a periphery of the body, a central wall extending from a first side of the peripheral frame portion to a second side of the peripheral frame portion, and a first helical bone contacting member attached to the body at the central wall and disposed within the superior half of the implant. The implant may further include a first support member attached to the body at the central wall at a junction coincident with the first helical bone contacting member and extending to a central region of the implant internal to the first helical bone contacting member. In addition, the implant may include a non-helical bone contacting member extending from a portion of the first support member that is disposed internal to the first helical bone contacting member.

In another aspect, the present disclosure is directed to an implant having a body defining a transverse plane dividing the implant into a superior half and an inferior half, the implant having an anterior side and a posterior side. The implant may further include a peripheral frame portion defining a periphery of the body and a central wall extending from a first side of the peripheral frame portion to a second side of the peripheral frame portion. The implant may also include a plurality of helical bone contacting members extending from a first side of the central wall to the peripheral frame portion and defining outer surfaces of the implant, the plurality of helical bone contacting members including: a superior anterior helical bone contacting member defining outer surfaces of the implant in the superior half of the implant and toward the anterior side of the implant; a superior posterior helical bone contacting member defining outer surfaces of the implant in the superior half of the implant and toward the posterior side of the implant; an inferior anterior helical bone contacting member defining outer surfaces of the implant in the inferior half of the implant and toward the anterior side of the implant; and an inferior posterior helical bone contacting member defining outer surfaces of the implant in the inferior half of the implant and toward the posterior side of the implant. In addition, the implant may include a first support member extending from a junction between the central wall and the superior anterior helical bone contacting member to a junction between the central wall and the inferior posterior helical bone contacting member. Further, the implant may include a second support member extending from a junction between the central wall and the superior posterior helical bone contacting member through a central region of the implant to a junction between the central wall and the inferior anterior helical bone contacting member. Also, the first support member and the second support member may intersect with one another at a first support member junction to form a substantially X-shaped member with the first support member junction disposed in the central region of the implant.

In another aspect, the present disclosure is directed to an implant having a body defining a transverse plane dividing the implant into a superior half and an inferior half, the implant having an anterior side and a posterior side and a peripheral frame portion lying substantially in the transverse plane and defining a periphery of the body. The implant may also include a first helical bone contacting member attached to the body and disposed within the superior half of the implant on a posterior side of the implant. In addition, the implant may include a second helical bone contacting member attached to the body and disposed within the superior half of the implant on an anterior side of the implant. Further, the implant may include a first support member extending from a first point on a superior side of the peripheral frame portion to the first helical bone contacting member and further extending inwardly of the first helical bone contacting member into a central region of the implant and terminating at a second point on an inferior side of the peripheral frame portion adjacent to the first point from which the first support member extends. Also, the implant may include a second support member extending from a third point on the peripheral frame portion opposite the first point to the second helical bone contacting member and further extending inwardly of the bone contacting members and terminating at a fourth point on the peripheral frame portion. The first point and the second point on the peripheral frame portion are disposed on the posterior side of the implant and the third point and the fourth point are disposed on the anterior side of the implant. Also, the first support member and the second support member are substantially U-shaped and are connected to one another at the bottoms of the two U-shapes forming a support member junction in the central region of the implant inward of the bone contacting members. Further, the implant may include a non-helical bone contacting member extending from the support member junction in a superior direction to a bone contacting surface.

Other systems, methods, features and advantages of the embodiments will be, or will become, apparent to one of ordinary skill in the art upon examination of the following figures and detailed description. It is intended that all such additional systems, methods, features and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, with emphasis instead being placed upon illustrating the principles of the embodiments. Moreover, in the figures, like reference numerals designate corresponding parts throughout the different views.

DETAILED DESCRIPTION

Figure 1:
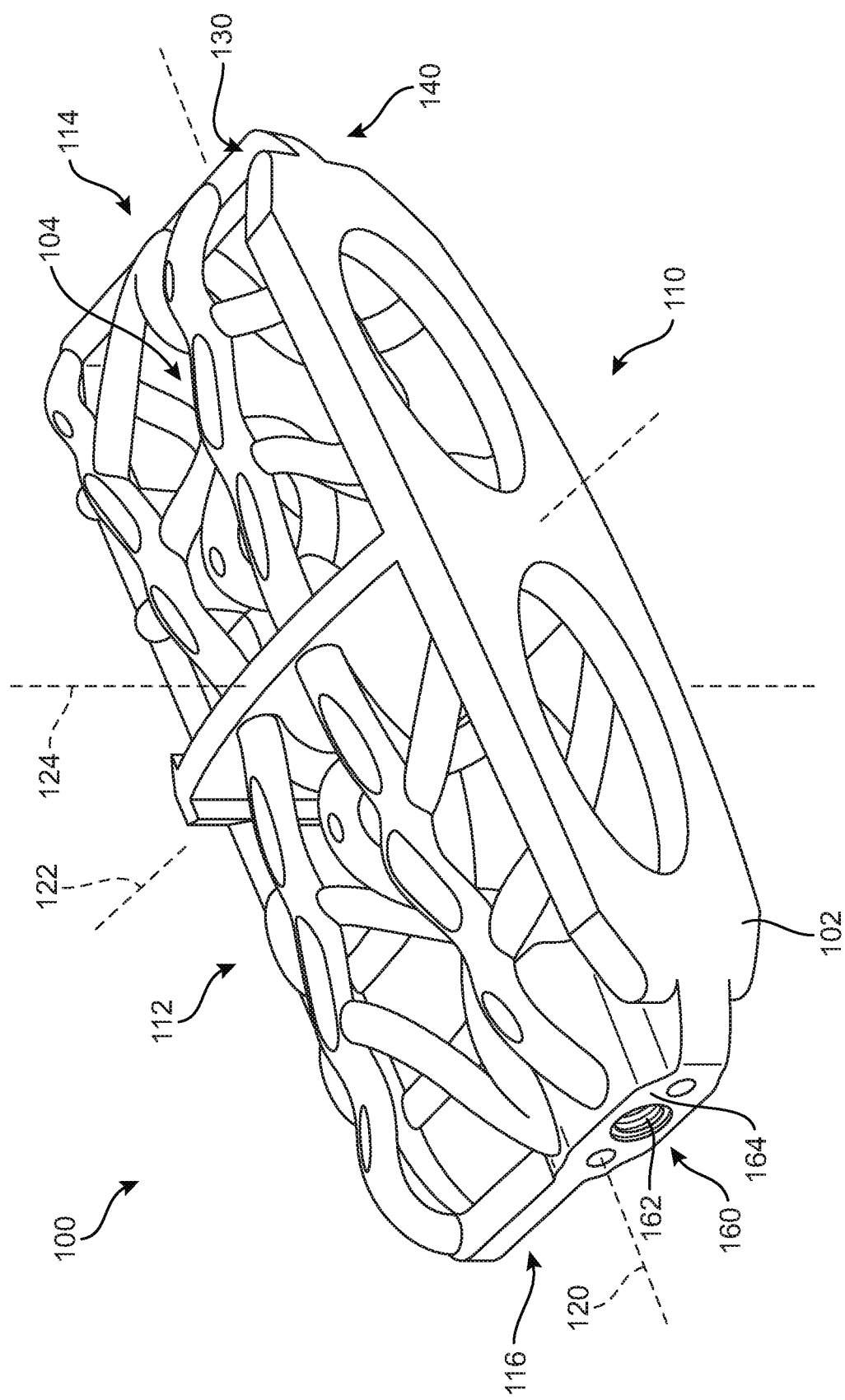
FIG. 1 is a schematic isometric superior view of an embodiment of an implant.

The embodiments described herein are directed to an implant for use in a spine. The embodiments include implants with a body and one or more structural members.

In addition to the various provisions discussed below, any of the embodiments disclosed herein may make use of any of the body/support structures, frames, plates, coils or other structures disclosed in McShane III et al., U.S. Publication Number 2018/0110626, published on Apr. 26, 2018, and titled "Implant with Protected Fusion Zones," and which is incorporated herein by reference in its entirety. For purposes of convenience, this application will be referred to throughout the present application as "The Protective Fusion Zones application."

Also, any of the embodiments disclosed herein may make use of any of the body/support structures, elements, frames, plates or other structures disclosed in McShane III et al., U.S. Publication Number 2017/0042697, published on Feb. 16, 2017, and titled "Implant with Arched Bone Contacting Elements," and which is incorporated herein by reference in its entirety.

Also, any of the embodiments disclosed herein may make use of any of the body/support structures, elements, frames, plates or other structures disclosed in McShane III et al., U.S. Publication Number 2018/0256351, published on Sep. 13, 2018, and titled "Implant with Structural Members Arranged Around a Ring," and which is incorporated herein by reference in its entirety and referred to herein as "The Ring application."

Also, any of the embodiments disclosed herein may make use of any of the body/support structures, elements, frames, plates, or other structures disclosed in Morris et al., U.S. Publication Number 2016/0324656, published on Nov. 10, 2016, and titled "Coiled Implants and Systems and Methods of Use Thereof," and which is incorporated herein by reference in its entirety and referred to herein as "The Coiled Implant Application."

Also, any of the embodiments disclosed herein may make use of any of the body/support structures, elements, frames, plates, or other structures disclosed in Nyahay et al., U.S. Publication Number 2018/0256352, published on Sep. 13, 2018, and entitled "Implant with Bone Contacting Elements Having Helical and Undulating Planar Geometries," and which is incorporated herein by reference in its entirety.

Also, any of the embodiments disclosed herein may make use of any of the body/support structures, elements, frames, plates, or other structures disclosed in Nyahay et al., U.S. Publication Number 2018/0256353, published on Sep. 13, 2018, and entitled "Corpectomy Implant," and which is incorporated herein by reference in its entirety.

Also, any of the embodiments disclosed herein may make use of any of the body/support structures, elements, frames, plates, or other structures disclosed in Bishop et al., U.S. Pat. No. 10,213,317, issued on Feb. 26, 2019, and entitled "Implant with Supported Helical Members," and which is incorporated herein by reference in its entirety.

Also, any of the embodiments disclosed herein may make use of any of the body/support structures, elements, frames, plates, or other structures disclosed in Stauffer et al., U.S. Publication Number 2019/0038428, published on Feb. 7, 2019, and entitled "Implant with a Diagonal Insertion Axis," and which is incorporated herein by reference in its entirety.

Also, any of the embodiments disclosed herein may make use of any of the body/support structures, elements, frames, plates, or other structures disclosed in Hamzey et al., U.S. Publication Number 2018/0296347, published on Oct. 18, 2018, and entitled "Implant with Curved Bone Contacting Elements," and which is incorporated herein by reference in its entirety.

Also, any of the embodiments disclosed herein may make use of any of the body/support structures, elements, frames, plates, or other structures disclosed in Hamzey et al., U.S. Publication Number 2018/0296350, published on Oct. 18, 2018, and entitled "Implant with Multi-Layer Bone Interfacing Lattice," and which is incorporated herein by reference in its entirety.

Figure 2:
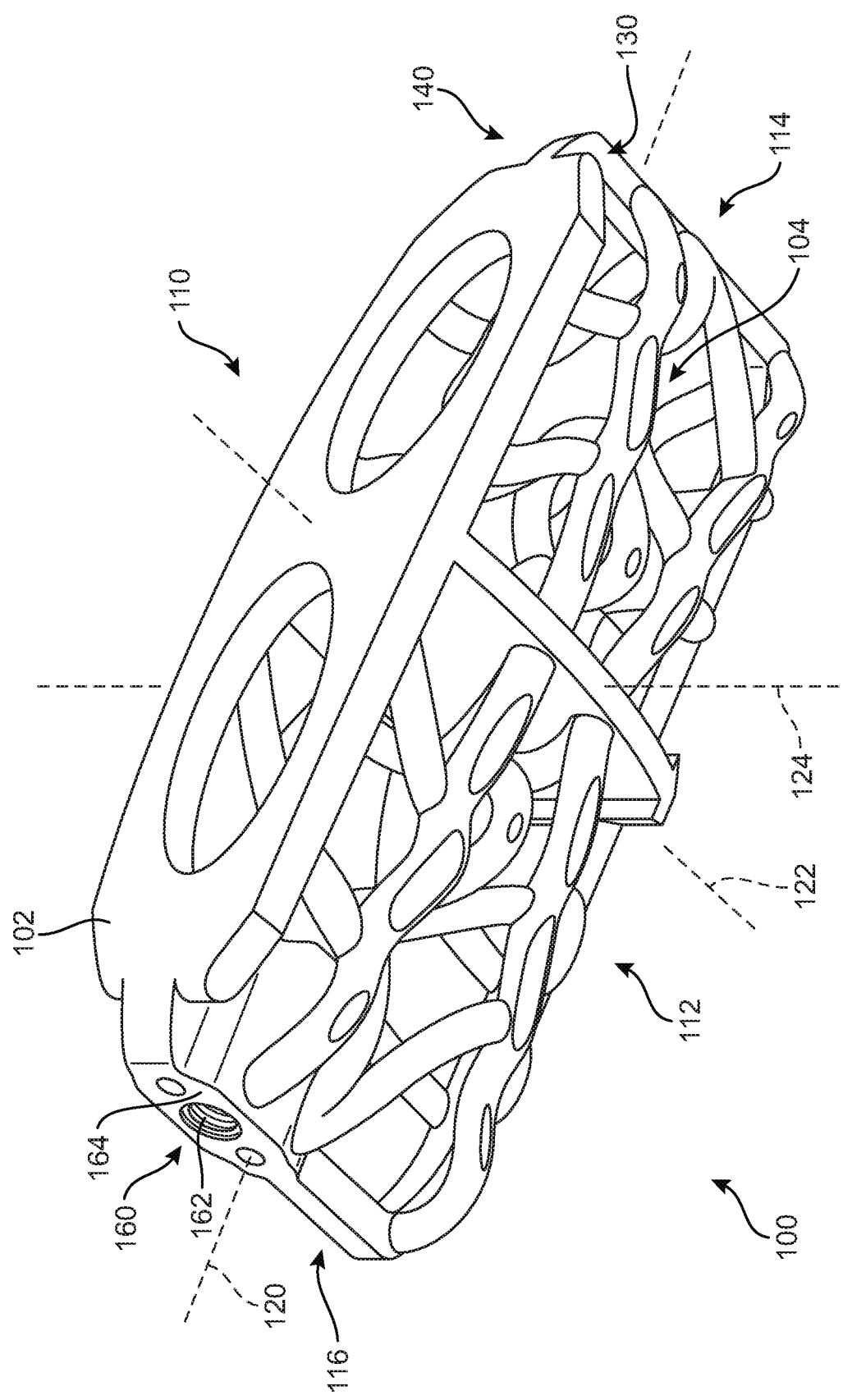
FIG. 2 is a schematic isometric inferior view of the implant of FIG. 1.

FIGS. 1 and 2 illustrate isometric views of an embodiment of an implant 100, which may be alternatively referred to as a device. Specifically, FIG. 1 is an isometric view of a top or superior side of implant 100, while FIG. 2 is an isometric view of a bottom or inferior side of implant 100. Implant 100 may also be referred to as a cage or fusion device. In some embodiments, implant 100 is configured to be implanted within a portion of the human body. In some embodiments, implant 100 may be configured for implantation into the spine. In some embodiments, implant 100 may be a spinal fusion implant, or spinal fusion device, that is inserted between adjacent vertebrae to provide support and/or facilitate fusion between the vertebrae.

In some embodiments, implant 100 may include a body 102. Body 102 may generally provide a frame or skeleton for implant 100. In some embodiments, implant 100 may also include a plurality of structural members 104. Plurality of structural members 104 may be fixedly attached to, and/or continuously formed (or "integrally formed") with, body 102. As used herein, the term "fixedly attached" shall refer to two components joined in a manner such that the components may not be readily separated (for example, without destroying one or both components).

As used herein, each structural member comprises a distinctive member or element that spans a portion of an implant. Structural members may overlap or intersect, similar to elements in a lattice or other 3D mesh structure. Some embodiments may use structural members in which the length of the member is greater than its width and its thickness. In embodiments where a structural member has an approximately circular cross-sectional shape, the structural member has a length greater than its diameter. In the embodiments seen in FIGS. 1-2, each structural member is seen to have an approximately rounded or circular cross-sectional shape (i.e., the member has the geometry of a solid tube). However, in other embodiments, a structural member could have any other cross-sectional shape, including, but not limited to, oval, various polygonal cross-sectional shapes, as well as any other regular and/or irregular cross-sectional shapes. In some cases, for example, the cross-sectional size and/or shape of a structural member could vary along its length (e.g., the diameter could change along its length).

For purposes of clarity, reference is made to various directional adjectives throughout the detailed description and in the claims. As used herein, the term "anterior" refers to a side or portion of an implant that is intended to be oriented towards the front of the human body when the implant has been placed in the body. Likewise, the term "posterior" refers to a side or portion of an implant that is intended to be oriented towards the back of the human body following implantation. In addition, the term "superior" refers to a side or portion of an implant that is intended to be oriented towards a top (e.g., the head) of the body while "inferior" refers to a side or portion of an implant that is intended to be oriented towards a bottom of the body. Reference is also made herein to "lateral" sides or portions of an implant, which are sides, or portions, facing along a lateral direction of the body (which correspond with the left or right sides of a patient).

In FIGS. 1-2, implant 100 is understood to be configured with an anterior side 110 and a posterior side 112. Implant 100 may also include a first lateral side 114 and a second lateral side 116 that extend between the posterior side 112 and the anterior side 110 on opposing sides of implant 100. Furthermore, implant 100 may also include a superior side 130 and an inferior side 140.

Reference is also made to directions or axes that are relative to the implant itself, rather than to its intended orientation with regards to the body. For example, the term "distal" refers to a part that is located further from a center of an implant, while the term "proximal" refers to a part that is located closer to the center of the implant. As used herein, the "center of the implant" could be the center of mass and/or a central plane and/or another centrally located reference surface.

An implant may also be associated with various axes. Referring to FIG. 1, implant 100 may be associated with a longitudinal axis 120 that extends along the longest dimension of implant 100 between first lateral side 114 and second lateral side 116. Additionally, implant 100 may be associated with a posterior-anterior axis 122 (also referred to as a "widthwise axis") that extends along the widthwise dimension of implant 100, between posterior side 112 and anterior side 110. Moreover, implant 100 may be associated with a vertical axis 124 that extends along the thickness dimension of implant 100 and which is generally perpendicular to both longitudinal axis 120 and posterior-anterior axis 122.

An implant may also be associated with various reference planes or surfaces. As used herein, the term "median plane" refers to a vertical plane which passes from the anterior side to the posterior side of the implant, dividing the implant into right and left halves, or lateral halves. As used herein, the term "transverse plane" refers to a horizontal plane located in the center of the implant that divides the implant into superior and inferior halves. As used herein, the term "coronal plane" refers to a vertical plane located in the center of the implant that divides the implant into anterior and posterior halves. In some embodiments, the implant is symmetric about two planes, such as the median and the transverse plane.

Embodiments can include provisions for texturing one or more surfaces of an implant. Such texturing can increase or otherwise promote bone growth and/or fusion to surfaces of the implant. In some embodiments, bone contacting members may be textured while support members may not be textured. This helps initial bone growth to be directed along the bone contacting members, rather than growing initially across support members. In other embodiments, however, support members could include surface texturing. In still further embodiments, one or more surfaces of a body could include surface texturing.

In some embodiments, the surface structure of one or more regions of an implant may be roughened or provided with irregularities. Generally, this roughened structure may be accomplished through the use of acid etching, bead or grit blasting, sputter coating with titanium, sintering beads of titanium or cobalt chrome onto the implant surface, as well as other methods. In some embodiments, the roughness can be created by 3D printing a raised pattern on the surface of one or more regions of an implant. In some embodiments, the resulting roughened surface may have pores of varying sizes. In some embodiments, pore sizes could range between approximately 0.2 mm and 0.8 mm. In one embodiment, pore sizes could be approximately 0.5 mm. In other embodiments, surface roughness comprising pore sizes less than 0.2 mm and/or greater than 0.8 mm are possible. The embodiments can make use of the surface texturing parts, features, processes or methods as disclosed in The Protected Fusion Zone Application. At least one exemplary texture is shown in Bishop et al., U.S. Pat. No. 10,213,317, issued on Feb. 26, 2019, and entitled "Implant with Supported Helical Members," and which is incorporated herein by reference in its entirety.

Some embodiments can include provisions that facilitate implantation, including insertion and/or fixation of the implant. In some embodiments, the implant may include a fastener receiving portion, which may be configured to receive a tool for holding the implant during implantation.

For example, as shown in FIG. 2, implant 100 may include a fastener receiving portion 160. Fastener receiving portion 160 may include a threaded opening 162 and a reinforced collar 164 to support threaded opening 162. In some embodiments, threaded opening 162 may be configured to receive a tool with a corresponding threaded tip to facilitate implantation of implant 100. In some embodiments, threaded opening 162 may be used with a screw to help attach implant 100 to a bone or another fixation device. In other embodiments, any other features for receiving fasteners and/or implantation tools could be incorporated into implant 100.

In some embodiments, an implant can be configured with one or more symmetries. In some cases, an implant may have a mirrored symmetry about one or more reference planes.

In some embodiments, implant 100 may include at least one axis of mirror symmetry. For example, as shown in FIG. 2, which illustrates an inferior perspective view of the implant shown in FIG. 1, in some embodiments, inferior side 140 of implant 100 may be a substantial mirror image of superior side 130. This orientation is defined for implantation from the right side of the body. That is, an insertion tool, such as a long rod-like handle may be inserted into fastener receiving portion 160 on the right side of the implant. Then the handle may be used to insert the implant into the body via a right side (of the body) access pathway.

Since implant 100 may have vertical symmetry wherein superior side 130 is the substantial mirror image of inferior side 140, implant 100 may be flipped such that the superior side is on the bottom and the inferior side is on the top. In such an orientation, implant 100 may be inserted via a left side (of the body) access route.

Figure 3:
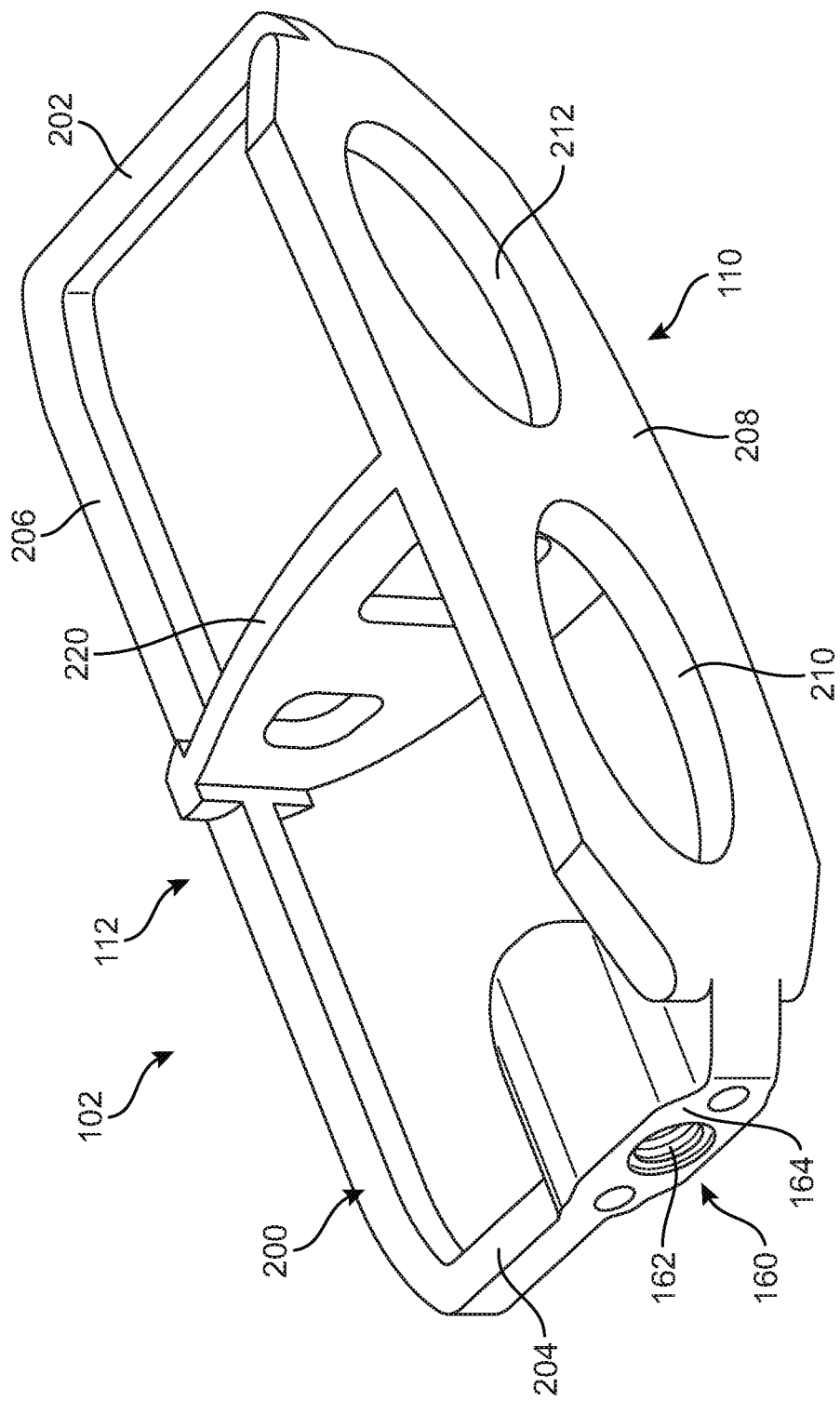
FIG. 3 is a schematic isometric superior view of a peripheral frame portion of the implant of FIG. 1 shown in isolation.

FIG. 3 illustrates a schematic isometric view of body 102 in isolation, with plurality of structural members 104 removed for purposes of clarity. In some embodiments, a body could include distinct frame portions that are oriented in different directions. In the embodiment shown in FIG. 3, body 102 includes a peripheral frame portion 200, also referred to as simply "peripheral portion 200". In some embodiments, peripheral portion 200 has a longest dimension aligned with longitudinal axis 120 and a widthwise dimension (e.g., the second longest dimension) aligned with posterior-anterior axis 122 of implant 100 (see FIGS. 1 and 2). Peripheral frame portion 200 comprises a first lateral frame portion 202, a second lateral frame portion 204 and a posterior frame portion 206, which primarily lie in the transverse plane.

In some embodiments, one or more sides of an implant (including lateral sides and/or anterior/posterior sides) could include a vertically oriented peripheral frame portion. In the embodiment of FIG. 3, body 102 is seen to include a vertically oriented peripheral frame portion 208 disposed at anterior side 110, which may also be referred to as an "anterior wall" of implant 100. In contrast, posterior side 112 lacks any frame portion or wall that extends vertically beyond the thickness of peripheral portion 200 in the embodiments of FIGS. 3-4. The presence of vertically oriented peripheral frame portion 208 may improve support and strength against vertical loads applied along the anterior side of the spine.

Although the present embodiment uses a vertically oriented frame or wall on the anterior side of implant 100, in other embodiments, a vertically oriented frame or wall could be located on the posterior side of implant 100 and/or on a lateral side of implant 100. In still other embodiments, the implant may lack any vertical walls along its perimeter (i.e., along the posterior, anterior or lateral sides).

As shown in FIG. 3, body 102 of implant 100 may include a central wall 220 which extends between vertically oriented peripheral frame portion 208 and posterior frame portion 206.

Figure 4:
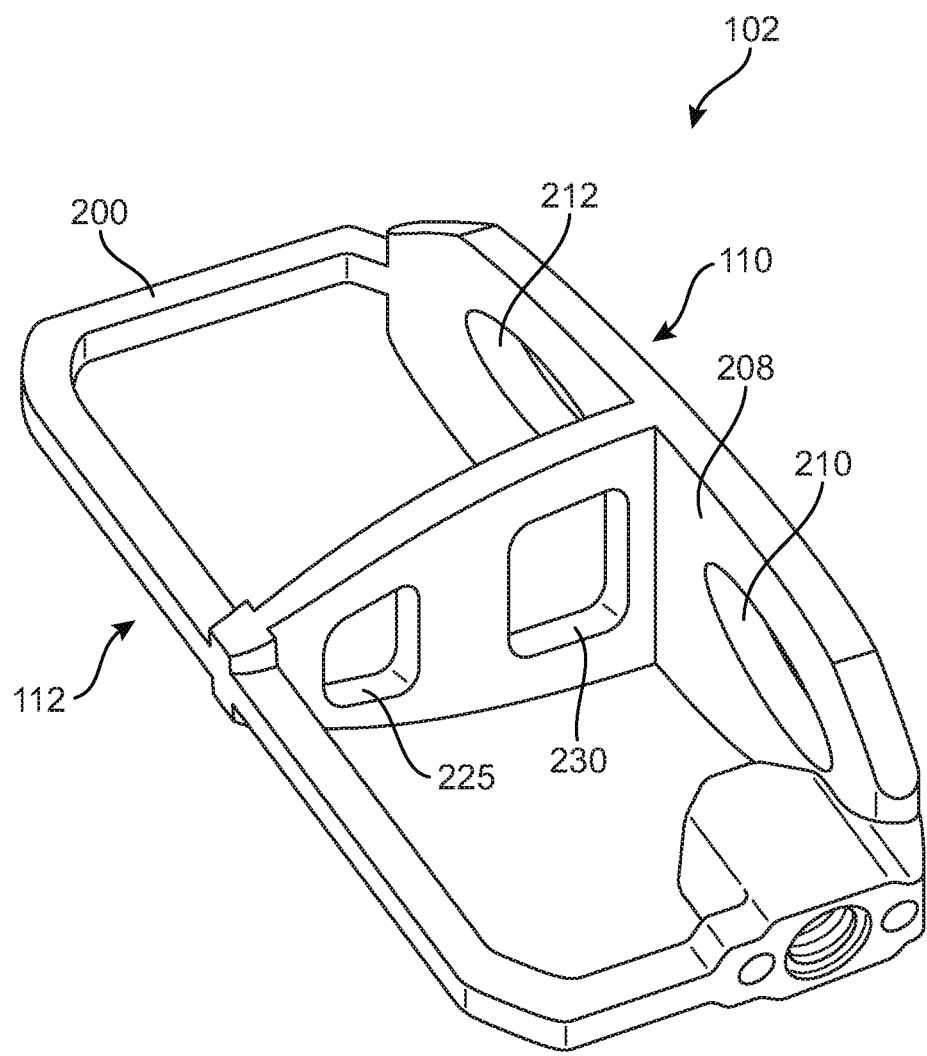
FIG. 4 is a schematic perspective lateral view of the peripheral frame portion of the implant of FIG. 1 shown in isolation.

FIG. 4 is a schematic perspective lateral view of an embodiment of implant 100. In some embodiments, vertically oriented peripheral frame portion 208 could include openings. In other embodiments, vertically oriented peripheral frame portion 208 may not include openings. In some embodiments, openings in a frame portion could provide an access point for inserting bone graft material or BGPM into an interior of an implant. The number, size and/or shape of openings in vertically oriented peripheral frame portion 208 could vary. In some cases, three or more openings could be used. In other cases, two openings could be used. In still other cases, a single opening could be used. Exemplary shapes for openings that could be used include, but are not limited to, rounded openings, rectangular openings, polygonal openings, regular openings and/or irregular openings. In the embodiment of FIGS. 3-4, vertically oriented peripheral frame portion 208 includes two large oval-shaped windows that may facilitate insertion of bone graft material (or BGMP) into an interior of the implant. Specifically, vertically oriented peripheral frame portion 208 includes first window 210 and second window 212.

For purposes of reference, implant 100 may be split into a superior half and an inferior half. Here, the "superior half" of implant 100 includes the portions of body 102 and plurality of structural members 104 disposed above the transverse plane. Likewise, the "inferior half" of implant 100 includes the portions of body 102 and plurality of structural members 104 disposed below the transverse.

With respect to the transverse plane (which coincides generally with the plane defined by first lateral frame portion 202, second lateral frame portion 204, and posterior frame portion 206), it may be seen that the superior half of implant 100 mirrors the inferior half of implant 100, at least approximately. In some embodiments, this may include not only the geometry of the body but also the shape, size, and orientations of each structural member.

Moreover, with respect to the median plane (which approximately divides implant 100 into two lateral halves), it may be seen that two lateral halves mirror one another approximately on either side of central wall 220. This includes not only the geometry of the body but also the shape, size and orientations of each structural member.

In some embodiments, central wall 220 may include one or more structural features configured to house bone ingrowth promoting material. For example, as shown in FIG. 4, in some embodiments, central wall 220 may include one or more thru-holes, such as a first thru-hole 225 and a second thru-hole 230.

An implant may include two or more kinds of structural members (or structural elements). In some embodiments, an implant can include one or more bone contacting structural members, or simply "bone contacting members." Bone contacting members may generally be substantially fully exposed on the outer surfaces of an implant, including along the superior and inferior sides of the implant. Thus, bone contacting members may be alternatively referred to as "outer members."

Figure 5:
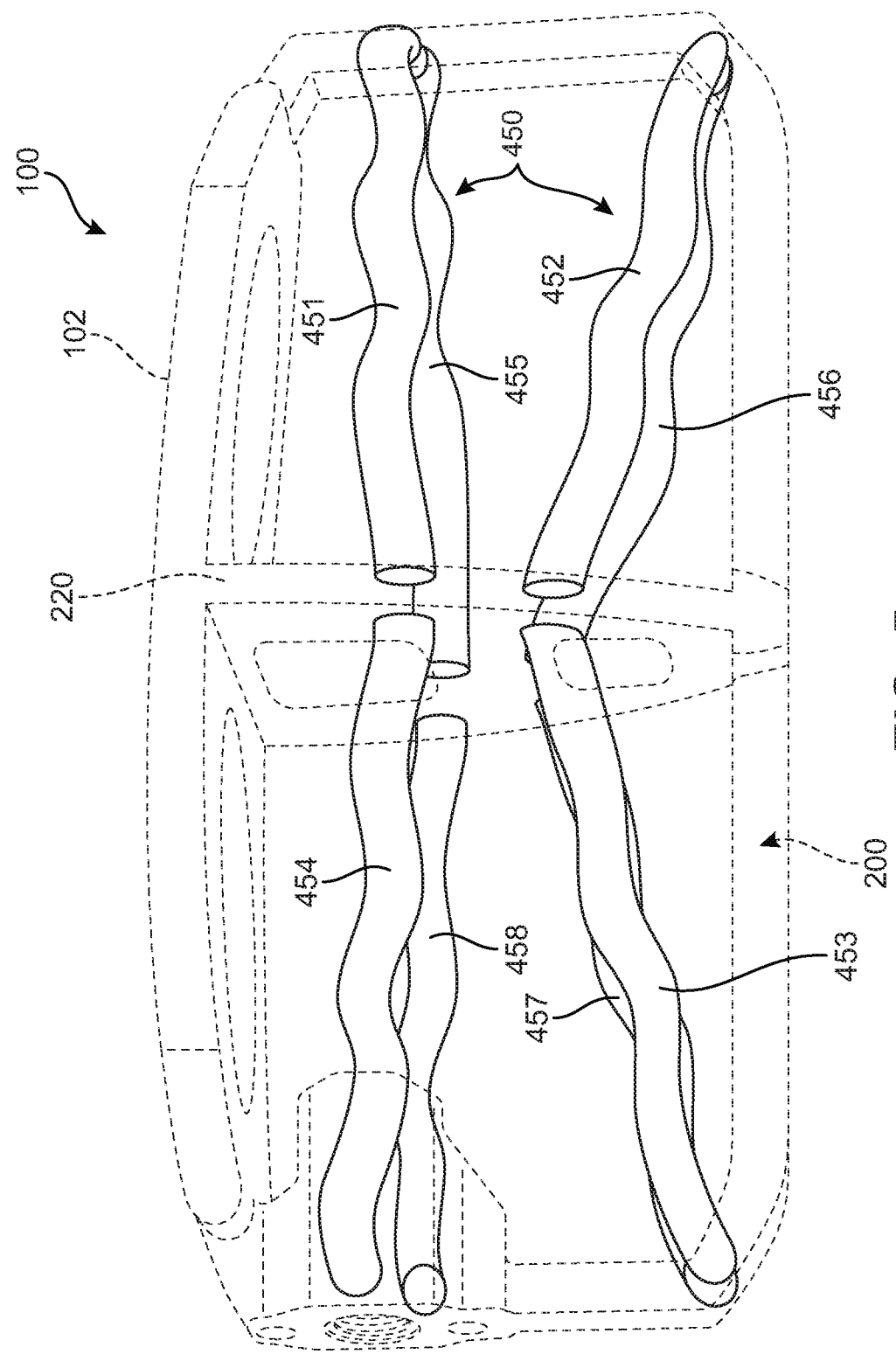
FIG. 5 is a schematic perspective view of helical bone contacting members of the implant of FIG. 1 with the peripheral frame portion shown in phantom.

FIG. 5 is a schematic perspective view of helical bone contacting members of the implant of FIG. 1 with peripheral frame portion 200 shown in phantom. As shown in FIG. 5, implant 100 may include a plurality of bone contacting members 450 attached to body 102. For example, bone contacting members 450 may include a first bone contacting member 451 attached to central wall 220 and extending to peripheral frame portion 200. As also shown in FIG. 5, implant 100 may include a second bone contacting member 452, a third bone contacting member 453, and a fourth bone contacting member 454, all of which may be disposed on the inferior half of implant 100. Similarly, implant 100 may also include a fifth bone contacting member 455, a sixth bone contacting member 456, a seventh bone contacting member 457, and an eighth bone contacting member 458, all of which may be disposed on the superior half of implant 100. As shown in FIG. 5, the arrangement of bone contacting members 450 may be generally symmetrical about central wall 220, as well as in the anterior-posterior direction. However, in some embodiments, bone contacting members 450 may be arranged in non-symmetrical configurations.

Embodiments may include provisions to minimize the number of bars or other supports needed, thereby increasing the interior volume available to receive new bone growth. In some embodiments, central wall 220 may have a larger thickness to provide reinforcement. For example, as shown in FIG. 5, central wall 220 may have a thickness that is greater than the thickness of the bone contacting members 450.

Helical Geometry of Outer Members

Embodiments can include provisions for protecting bone growth along and adjacent to bone contacting members of an implant. In some embodiments, a bone contacting member can be configured with a geometry that helps to protect new bone growth in selected regions or "protected fusion zones." In some embodiments, a bone contacting member can have a spiral, helical or twisted geometry that provide a series of such protected fusion zones for enhanced bone growth.

Some outer members may have a generalized helical geometry. As used herein, a "generalized helical geometry" or "spiraling geometry" refers to a geometry where a part (portion, member, etc.) winds, turns, twists, rotates or is otherwise curved around a fixed path. In some cases, the fixed path could be straight. In other cases, the fixed path can be curved. In the present embodiments, for example, the fixed path is generally a combination of straight segments and curved segments.

Figure 6:
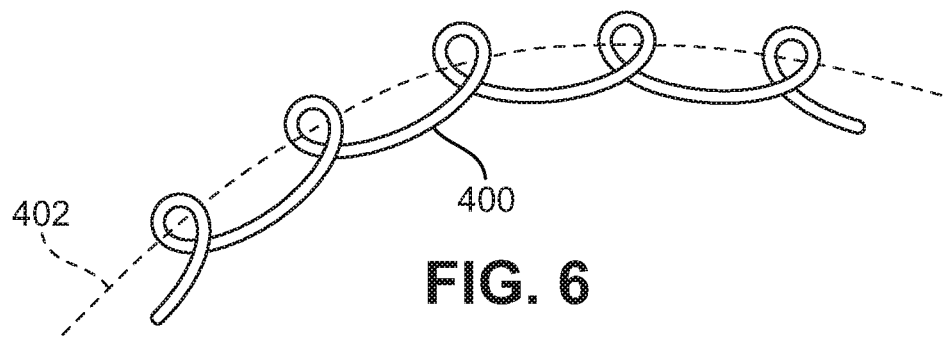
FIG. 6 is a schematic view of a curve with a generalized helical geometry, according to an embodiment.

FIG. 6 illustrates a schematic view of a curve 400 with a generalized helical geometry. Curve 400 is seen to wind around a fixed path 402 that is itself curved. In contrast to curve 400, however, fixed path 402 does not include any turns, windings, etc. An example of a helical curve with a straight fixed path is shown in FIG. 1 of the Coiled Implant Application.

Curves having a generalized helical geometry (also referred to as generalized helical curves) may be characterized by "coils," "turns," or "windings" about a fixed path. Exemplary parameters that may characterize the specific geometry of a generalized helical curve can include coil diameter (including both a major and minor diameter) and the pitch (i.e., spacing between adjacent coils). In some cases, the "amplitude" of a coil or loop may also be used to describe the diameter or widthwise dimension of the coil or loop. Each of these parameters could be constant or could vary over the length of a generalized helical curve.

Figure 7:
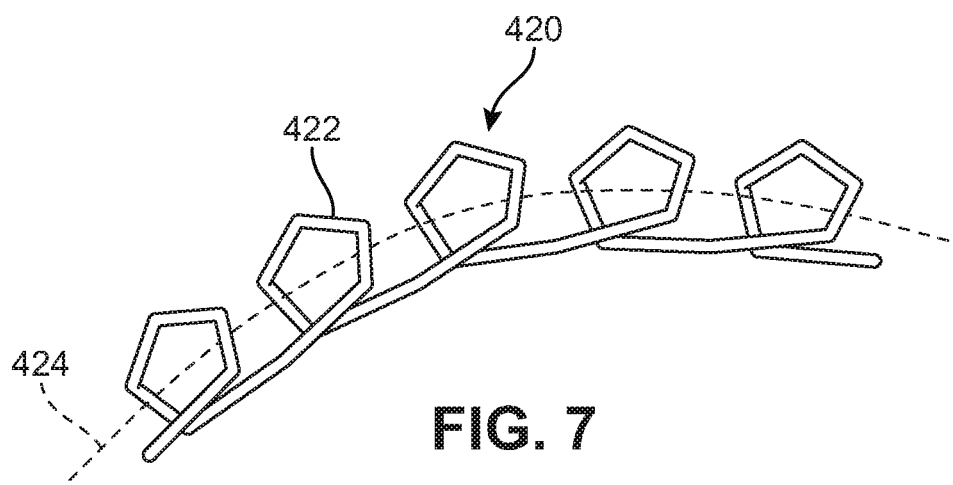
FIG. 7 is a schematic view of another curve with a generalized helical geometry, according to an embodiment.

Generalized helical curves need not be circular or even round. In some embodiments, for example, a generalized helical curve could have linearly-segmented shape (or locally polygonal shape) such that each "coil" or "turn" is comprised of straight line segments rather than arcs or other curved segments. An example of such a generalized helical curve is shown in FIG. 7. Referring to FIG. 7, generalized helical curve 420 is seen to be comprised of straight-line segments 422. The angles between adjacent segments are such that they wind or loop around a fixed path 424 in "polygonal coils."

Figure 8:
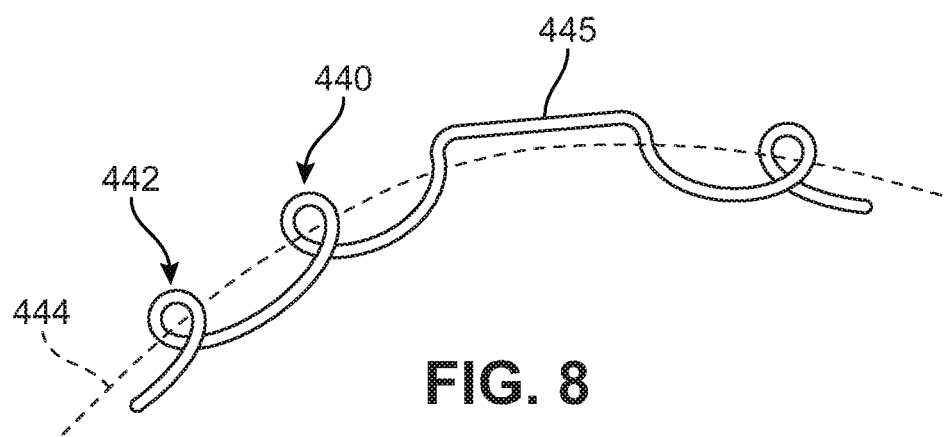
FIG. 8 is a schematic view of a curve with a generalized helical geometry including a straight segment, according to an embodiment.

Generalized helical curves may also include combinations of curved and straight segments. An example of such a combination curve is depicted in FIG. 8. Referring to FIG. 8, generalized helical curve 440 includes generally round (i.e., curved) coil segments 442 curing around a fixed path 444. In addition, curve 440 includes at least one straight-line segment 445 that extends between adjacent coils.

Although the generalized curves shown in FIGS. 6-8 are one-dimensional curves, similar principles may be applied to three-dimensional parts, including structural members.

For purposes of characterizing the geometry of one or more structural members, each structural member can be understood to have a "central member curve." The central member curve of each structural member may be defined as a curve that extends along the length of the structural member such that each point along the curve is centrally positioned within the structural member.

In embodiments where a structural member winds or loops around a fixed path with an amplitude or diameter that is much greater than the cross-sectional diameter of the structural member itself, the structural member may be wound into visible distinct coils. Such coils are discussed in thorough detail in the Coiled Implant Application. In other embodiments, however, a structural member could be wound around a fixed path with an amplitude or diameter that is less than the cross-sectional diameter of the structural member itself. In such a case the resulting geometry of a structural member may appear to be twisted, but the geometry may lack the distinct coils seen in the Coiled Implant Application. However, it may be appreciated that while the outermost surface of such a structural member may not exhibit distinct coils, the central member curve of the structural member does have such coils or turns and moreover has a clear generalized helical geometry.

Figure 9:
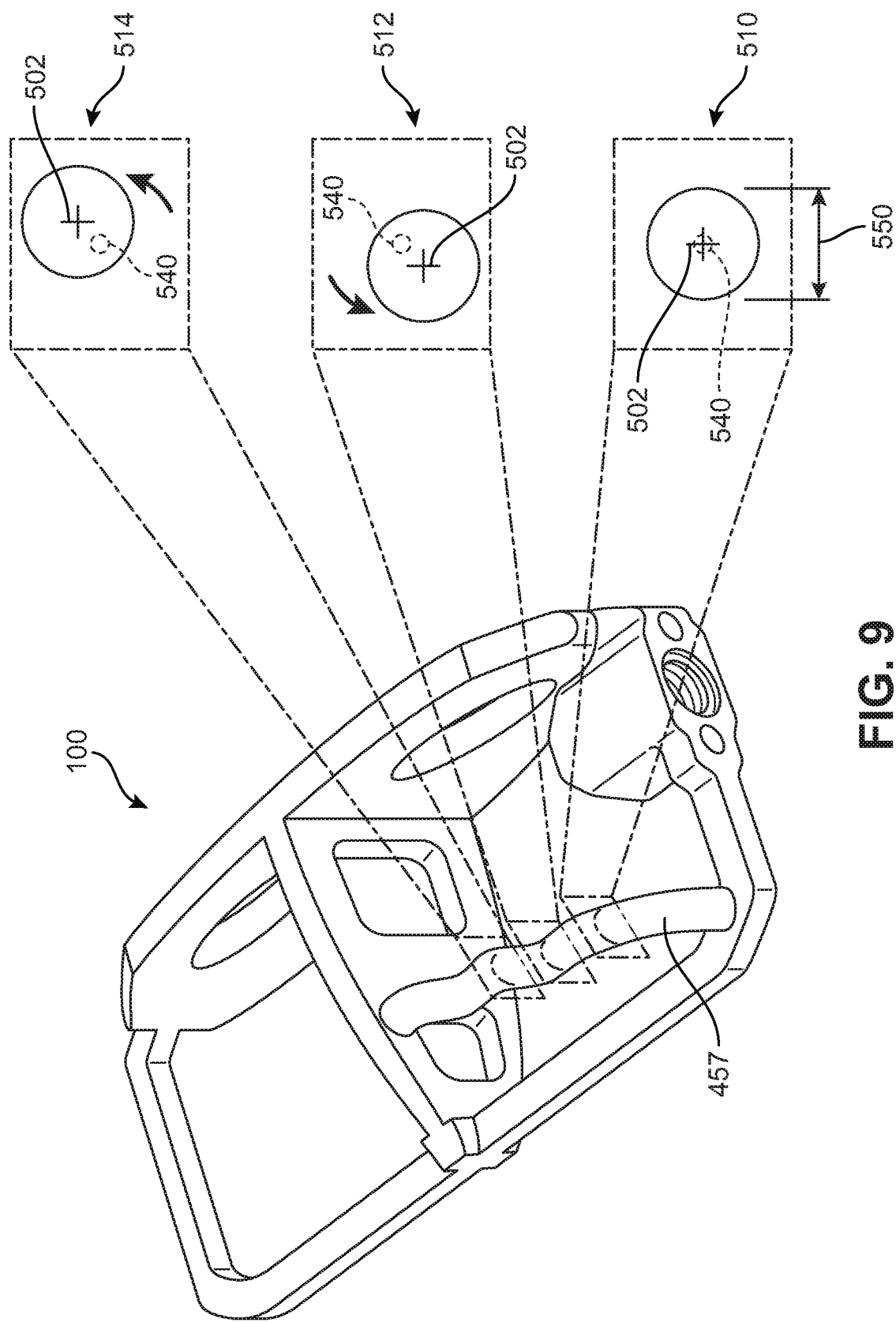
FIG. 9 is a schematic lateral perspective view of a portion of an implant with a helical bone contacting member shown in isolation so as to demonstrate the generalized helical geometry of the helical bone contacting member, according to an embodiment.
Figure 10:
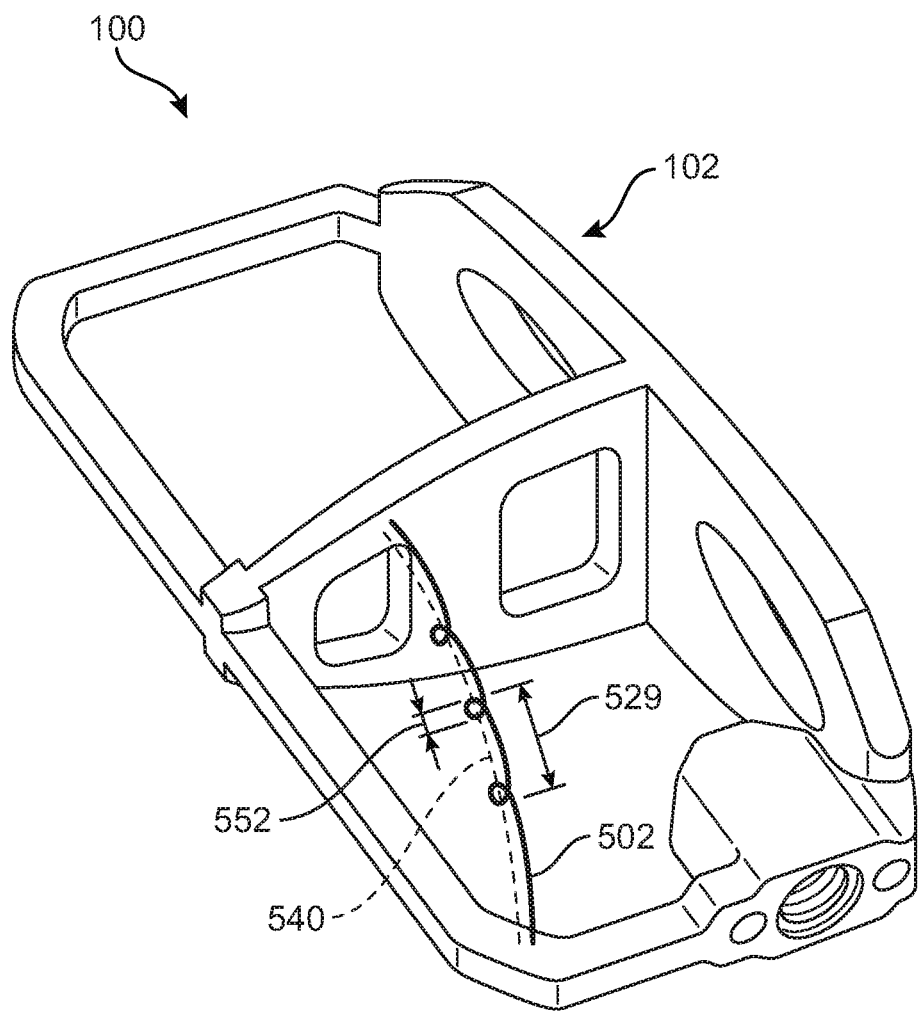
FIG. 10 is a schematic lateral perspective view of the implant of FIG. 1, including the central member curves of the structural members seen in FIG. 9.

FIGS. 9 and 10 illustrate an exemplary helical geometry of a structural member. FIG. 9 is a schematic perspective view of a portion of an implant with a helical bone contacting member shown in isolation so as to demonstrate the generalized helical geometry of the helical bone contacting member, according to an embodiment. FIG. 10 is a schematic perspective view of body 102 with all structural members removed for clarity, and with the helical path of the structural member of FIG. 9 diagrammed.

FIG. 9 illustrates implant 100 with a single bone contacting member 457 shown. The other structural members of implant 100 are not shown in FIG. 9 for purposes of clarity. As seen in FIG. 9, the outer surface of bone contacting member 457 exhibits a twisted geometry indicative of a spiral or helix.

As clearly seen in comparing FIGS. 9 and 10, the cross-sectional diameter 550 of bone contacting member 457 is greater than a corresponding winding diameter 552 of the coils or turns in central member curve 502. In other embodiments, the cross-sectional diameter of a bone contacting member could be less than a corresponding winding diameter of the coils or turns of its central member curve. In such an embodiment, the bone contacting member would be configured in a series of distinct coils.

Since the winding of the bone contacting member occurs with amplitude much smaller than the diameter 550 of the bone contacting member 457, the geometry of the part may be difficult to discern. In order to illustrate the winding, helical geometry of bone contacting member 457, FIG. 9 includes a sequence of cross-sectional views taken along bone contacting member 457.

The generalized helical geometry of bone contacting member 457 becomes much clearer when the geometry of its central member curve 502 (which is clearly shown in FIG. 10) is considered as it winds around a fixed path 540. (Fixed path 540 is also shown in FIG. 10. It may be understood that fixed path 540 represents the "average" or approximate path of bone contacting member 457 that ignores the helical deviations at some segments).

In a first cross-sectional view of a first portion 510 of bone contacting member 457, a first point (indicated using a cross in FIG. 9) of central member curve 502 is seen to be approximately aligned with a corresponding point (indicated using a circle) of fixed path 540. At a second portion 512 of bone contacting member 457, a second point of central member curve 502 is seen to be positioned at a first rotational position away from a corresponding point of fixed path 540. At a third portion 514, a third point of central member curve 502 is seen to be positioned at a second rotational position from a corresponding point of fixed path 540. Thus, it can be seen that, as bone contacting member 457 twists with a small amplitude along its extension, central member curve 502 indeed winds or spirals around fixed path 540.

With further reference to FIGS. 9 and 10, bone contacting member 457 does not have a generalized helical geometry through its entire length. Instead, its central member curve is configured with a winding segment where the central member curve completes several full turns (three in FIGS. 9-10) around a fixed path. Away from the winding segment, its central member curve may not include any turns, twists, etc.

Although the present embodiment includes at least one outer member with a winding segment that makes one or more full turns around a fixed path, other embodiments could be configured with central member curves that only make partial turns around a fixed path.

While the description here has focused on the geometry of a single bone contacting member 457, it may be appreciated that some or all of the remaining outer members in plurality of structural members 104 may have a similar generalized helical geometry. It may be further appreciated that two different bone contacting members could have slightly different geometries, with distinct bone contacting member curves that include variations in the number of windings, shape of the windings, etc.

In some embodiments, an implant can include bone contacting members that are locally helical over small distances compared to the length, width or height of the implant. For example, implant 100 may be characterized as having bone contacting members that are locally helical or locally spiraling, rather than globally helical. In particular, each bone contacting member of implant 100 is bounded within a single quadrant of implant 100 and does not cross the transverse plane or the median plane of implant 100. Thus, a full turn of the outer members is accomplished over distances that are much smaller than half the length, width or height of the implant. This allows multiple windings within each quadrant of the implant and also results in the pitch between windings being smaller than the length, width or height of the implant. For example, in FIG. 10, central member curve 502 has a pitch 529 between adjacent windings or turns that is less than one third of the length of bone contacting member 457. Pitch 529 is also less than one tenth of the length of implant 100. This relatively small pitch size allows for a greater number of proximal surface regions along each bone contacting member, thereby increasing the number of bone contacting surfaces of the inferior and superior surfaces of implant 100.

In some embodiments, an implant can include one or more structural members that provide support to one or more bone contacting members. Such supporting structural members may be referred to as "support members." In some embodiments, at least some portions of each support member may be generally disposed inwardly of the bone contacting members.

Figure 11:
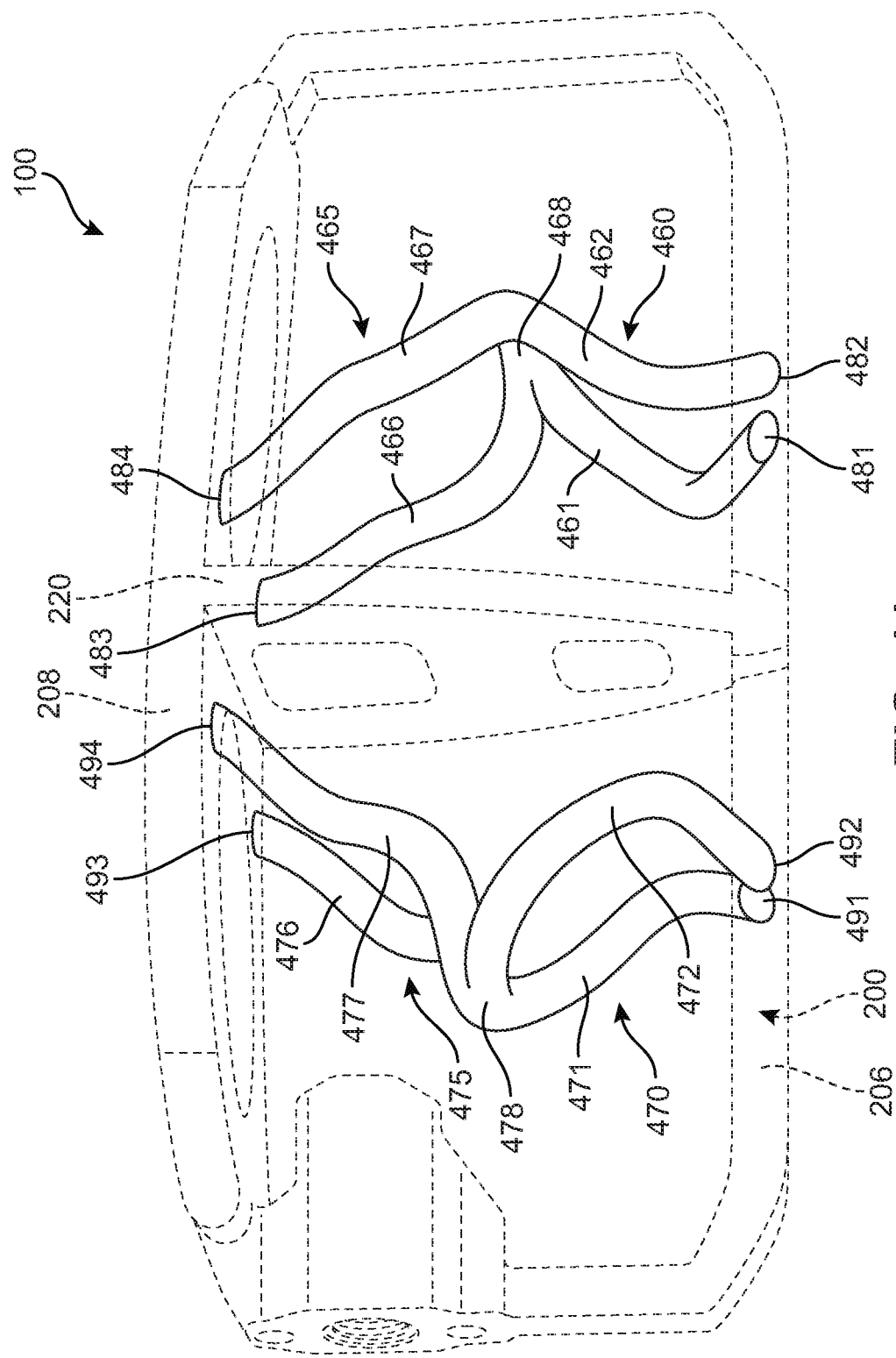
FIG. 11 is a schematic perspective view of a plurality of support members arranged within the body of the implant of FIG. 1, with the peripheral frame portion shown in phantom.

FIG. 11 is a schematic perspective view of a plurality of support members arranged within the body of implant 100, with peripheral frame portion 200 shown in phantom. As shown in FIG. 11, implant 100 may include a first support member 460, including a first leg 461 extending from a first point 481 on a superior side of peripheral frame portion 200 to a bone contacting member (see FIG. 13) and further extending inwardly of the bone contacting member into a central region of the implant and extending down a second leg 462 terminating at a second point 482 on an inferior side of peripheral frame portion 200 adjacent to first point 481 from which first support member 460 extends.

As further shown in FIG. 11, implant 100 may include a second support member 465 extending from a third point 483 on peripheral frame portion 200 opposite first point 481 along a first leg 466 to a bone contacting member (see FIG. 13) and further extending inwardly of the bone contacting members and extending along a second leg 467 and terminating at a fourth point 484 on peripheral frame portion 200. As shown in FIG. 11, in some embodiments, first point 481 and second point 482 on peripheral frame portion 200 may be disposed on the first side of implant 100 and third point 483 and fourth point 484 may be disposed on the second side of implant 100.

In some embodiments, the support members may be substantially U-shaped. For example, as shown in FIG. 11, first support member 460 and second support member 465 may be substantially U-shaped. Also, in some embodiments, the support members may be connected to one another. For example, as shown in FIG. 11, first support member 460 and second support member 465 may be connected to one another at the bottoms of the two U-shapes, in an overlapping region 468 in the central region of the implant inward of the bone contacting members.

In some embodiments, at least one of first support member 460 and second support member 465 may include one or more bone contacting portions. For example, as shown in FIG. 11, first leg 461, second leg 462, first leg 466, and second leg 467 of first support member 460 and second support member 465 may be exposed to the outside of implant 100, and thus, may include bone contacting portions.

As shown in FIG. 11, implant 100 may include a third support member 470, including a first leg 471 extending from a first point 491 on a superior side of peripheral frame portion 200 to a bone contacting member (see FIG. 13) and further extending inwardly of the bone contacting member into a central region of the implant and extending down a second leg 472 terminating at a second point 492 on an inferior side of peripheral frame portion 200 adjacent to first point 491 from which first support member 470 extends.

As shown in FIG. 11, implant 100 may include a fourth support member 475, including a first leg 476 extending from a first point 493 on a superior side of peripheral frame portion 200 to a bone contacting member (see FIG. 13) and further extending inwardly of the bone contacting member into a central region of the implant and extending down a second leg 477 terminating at a second point 494 on an inferior side of peripheral frame portion 200 adjacent to first point 493 from which first support member 475 extends.

As shown in FIG. 11, third support member 470 and fourth support member 475 may be substantially U-shaped. Also, in some embodiments, the support members may be connected to one another. For example, as shown in FIG. 11, third support member 470 and fourth support member 475 may be connected to one another at the bottoms of the two U-shapes, at a junction 478 in the central region of the implant inward of the bone contacting members.

Figure 12:
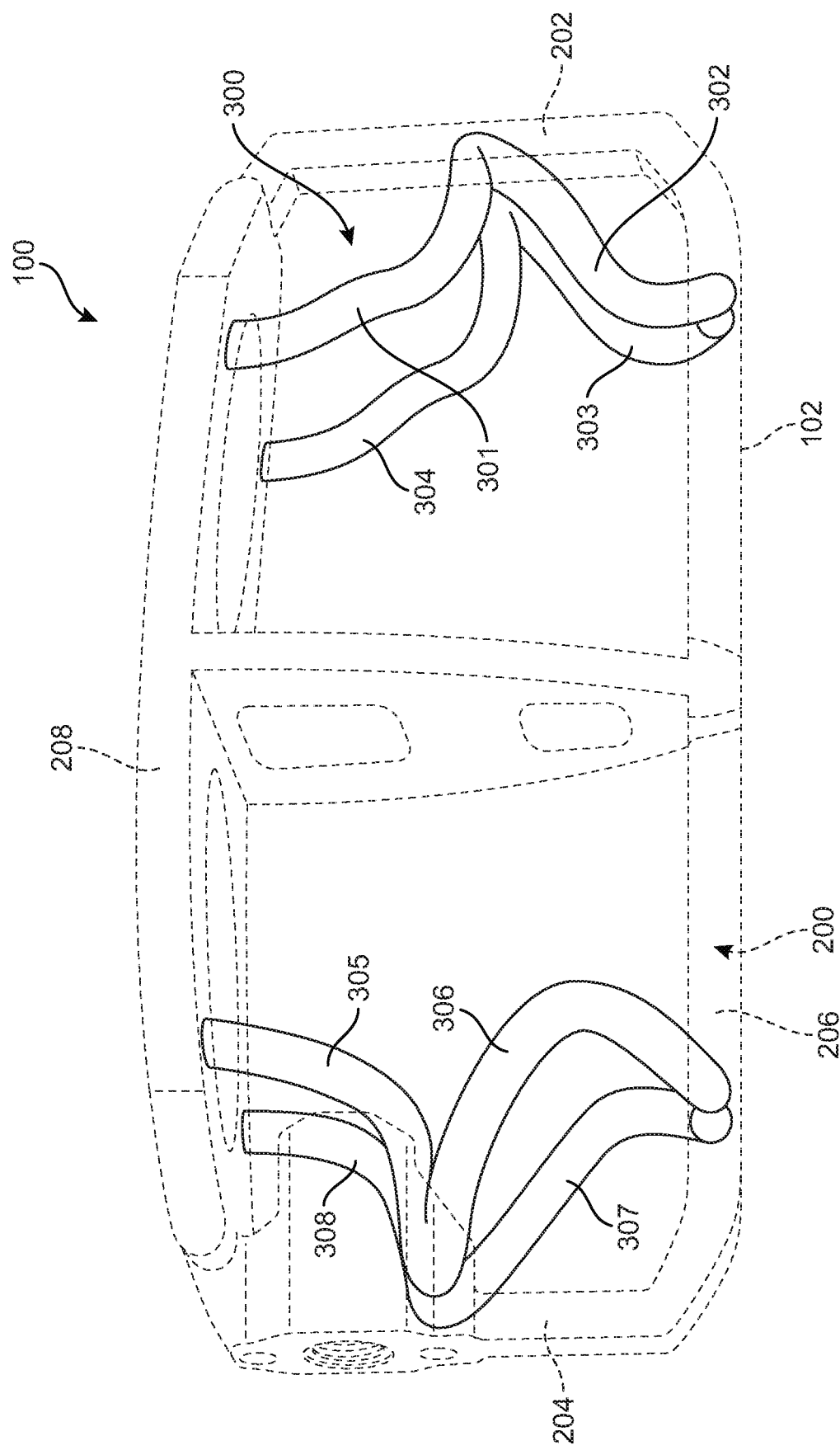
FIG. 12 is a schematic perspective view of a plurality of corner braces arranged within the body of the implant of FIG. 1, with the peripheral frame portion shown in phantom.

Additional structural members may also be provided. For example, in some embodiments, corner braces may be provided to reinforce the implant. FIG. 12 is a schematic perspective view of a plurality of corner braces 300 arranged within the body 102 of implant 100, with peripheral frame portion 200 shown in phantom. As shown in FIG. 12, a first corner brace 301 may extend from vertically oriented peripheral frame portion 208 to first lateral frame portion 202 on an inferior half of implant 100. A second corner brace 302 may extend from first lateral frame portion 202 to posterior frame portion 206 on the inferior half of implant 100. A third corner brace 303 may extend from first lateral frame portion 202 to posterior frame portion 206 on the superior half of the implant. Also, a fourth corner brace 304 may extend from vertically oriented peripheral frame portion 208 to first lateral frame portion 202 on the superior half of implant 100.

At the opposite lateral end of implant 100, a four more corner braces may be arranged similarly. For example, as shown in FIG. 12, a fifth corner brace 305 may extend from vertically oriented peripheral frame portion 208 to first lateral frame portion 202 on an inferior half of implant 100. A sixth corner brace 306 may extend from first lateral frame portion 202 to posterior frame portion 206 on the inferior half of implant 100. A seventh corner brace 307 may extend from first lateral frame portion 202 to posterior frame portion 206 on the superior half of the implant. Also, an eighth corner brace 308 may extend from vertically oriented peripheral frame portion 208 to first lateral frame portion 202 on the superior half of implant 100.

In different embodiments, the sizes, configurations, and orientations of bone contacting members, support members, and/or corner braces could vary. FIGS. 13-24 illustrate various aspects of the structural members in the interior region of the implant. FIGS. 13-19 are a sequence of illustrations in which more structural members are added to each successive figure in order to show the inner structure of the implant and the relationships between the support members and the bone contacting members.

Figure 13:
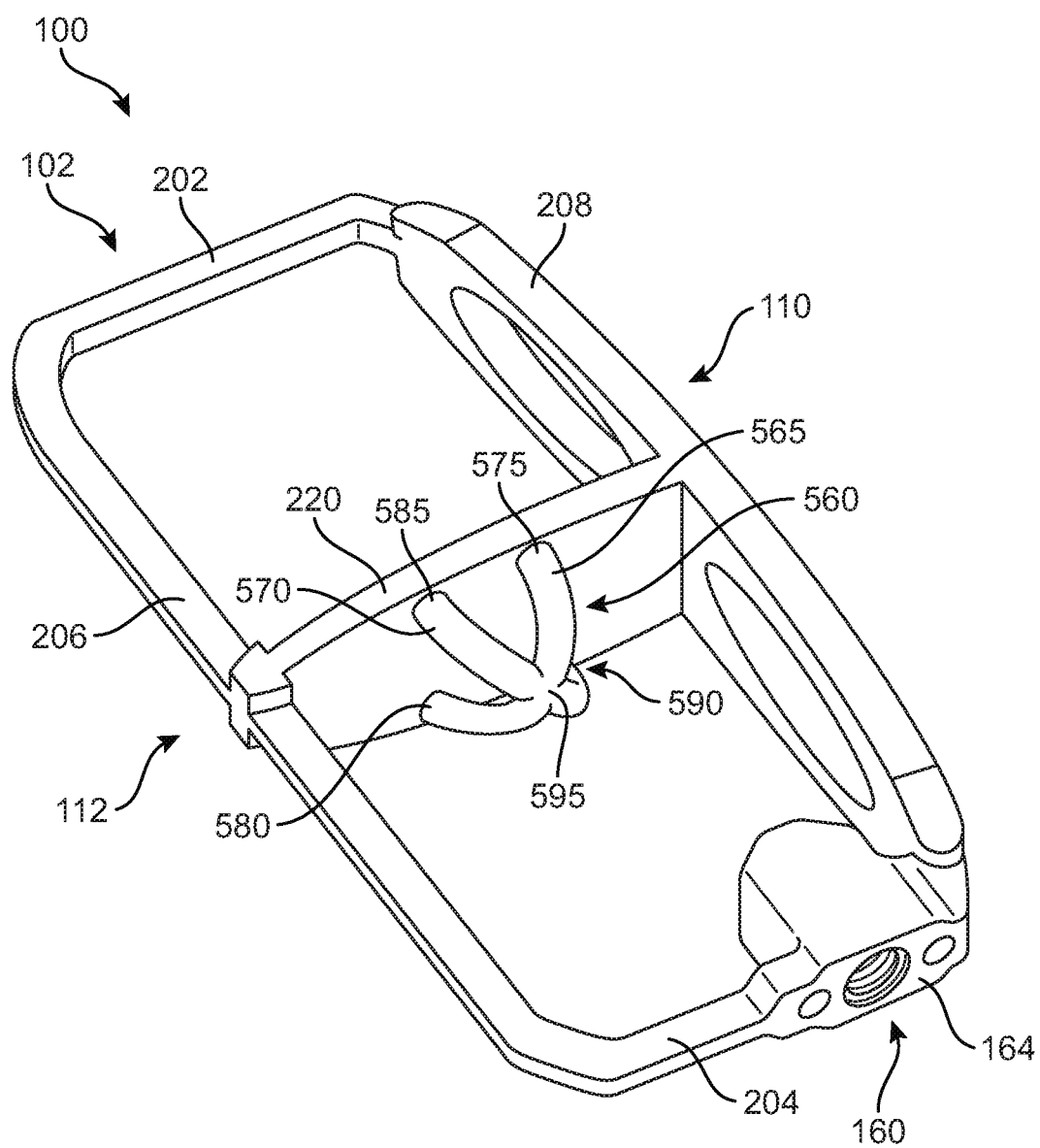
FIG. 13 is a schematic perspective lateral view of an implant with structural members removed and revealing support members in an X-shaped arrangement.

FIG. 13 is a schematic perspective lateral view of an implant with structural members removed and revealing support members having an X-shaped arrangement, thus forming an x-shaped support structure such as an x-shaped member. FIG. 13 shows implant 100. For clarity, no bone contacting members are shown in FIG. 13. FIG. 13 illustrates body 102 having anterior side 110, posterior side 112, first lateral frame portion 202, second lateral frame portion 204, posterior frame portion, and vertically oriented peripheral frame portion 208. FIG. 13 also shows central wall 220.

As shown in FIG. 13, implant 100 may include a substantially X-shaped member formed of two intersecting support members attached to central wall 220. For example, implant 100 may include a first support member 565 extending from a junction 575 at central wall 220 in a superior anterior portion of implant 100 to a junction 580 at central wall 220 in an inferior posterior portion of implant 100. A second support member 570 extending from a junction 585 at central wall 220 in a superior posterior portion of implant 100 to a junction 590 at central wall 220 in an inferior anterior portion of implant 100. First support member 565 intersects with second support member 570 in a support member junction 595 in the central region of implant 100 inward of the helical bone contacting members to form substantially X-shaped member 560.

Figure 14:
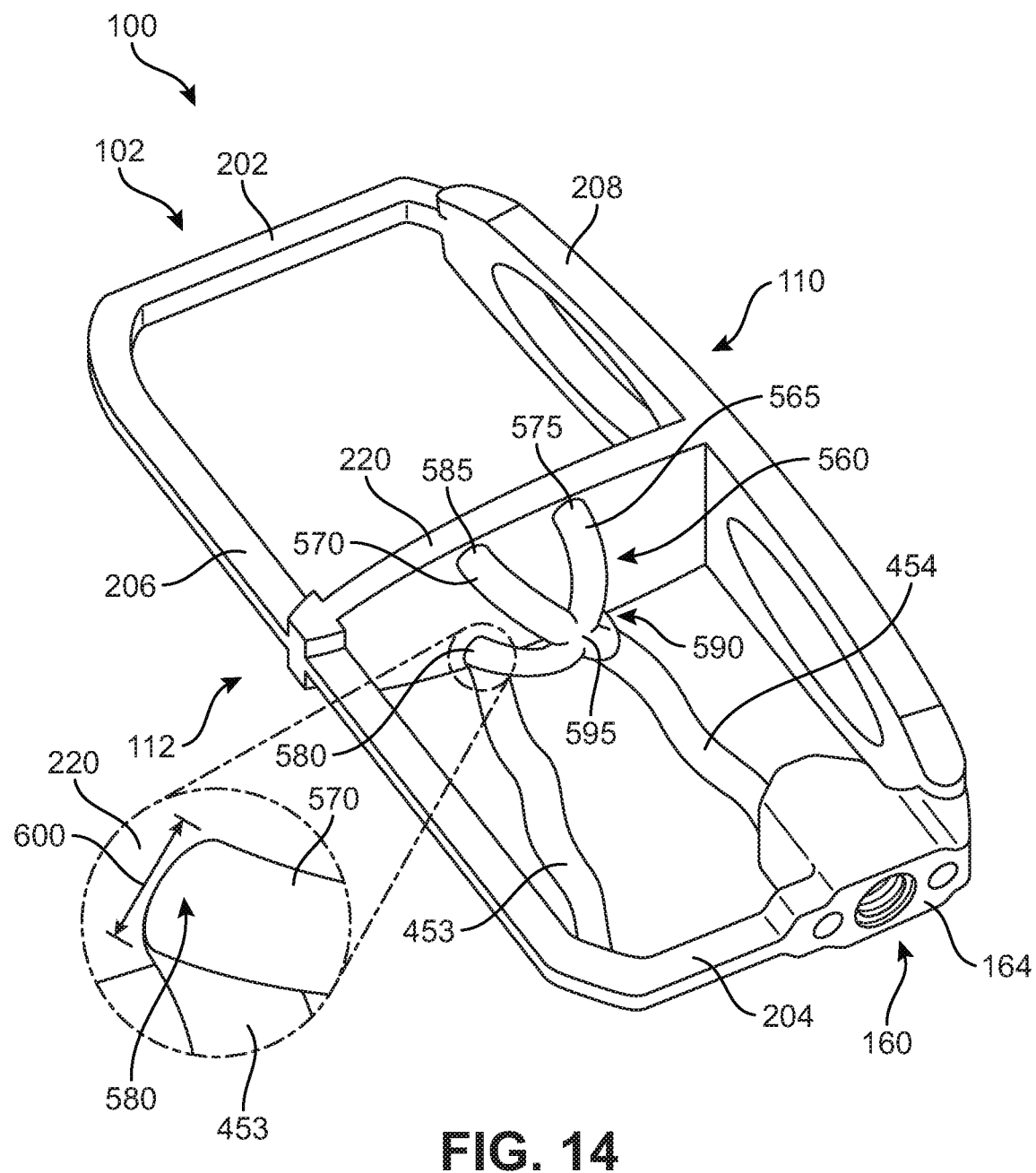
FIG. 14 is a schematic perspective lateral view of an implant as shown in FIG. 13, with helical bone contacting members added in the inferior half of the implant.

FIG. 14 is a schematic perspective lateral view of an implant as shown in FIG. 13, with helical bone contacting members added in the inferior half of the implant. FIG. 14 illustrates helical bone contacting member 454 in the inferior anterior portion of implant 100. In addition, FIG. 14 illustrates helical bone contacting member 453 in the inferior posterior portion of implant 100.

As shown in the enlarged portion of FIG. 14, support member 565 may be fixedly attached to central wall 220 at junction 580 coincident with helical bone contacting member 453. For purposes of this disclosure, the term coincident shall be defined as follows. At junction 580, support member 565 and bone contacting member 453 may have the same general size 600 (e.g., diameter) and may be fully aligned with one another at the location where both members attach to central wall 220. Further, in some embodiments, support member 565 and bone contacting member 453 may have the same cross-sectional shape and occupy the same location at central wall 220.

In addition, as also shown in FIG. 14, support member 570 may be attached to central wall 220 at junction 590 coincident with helical bone contacting member 454.

Figure 15:
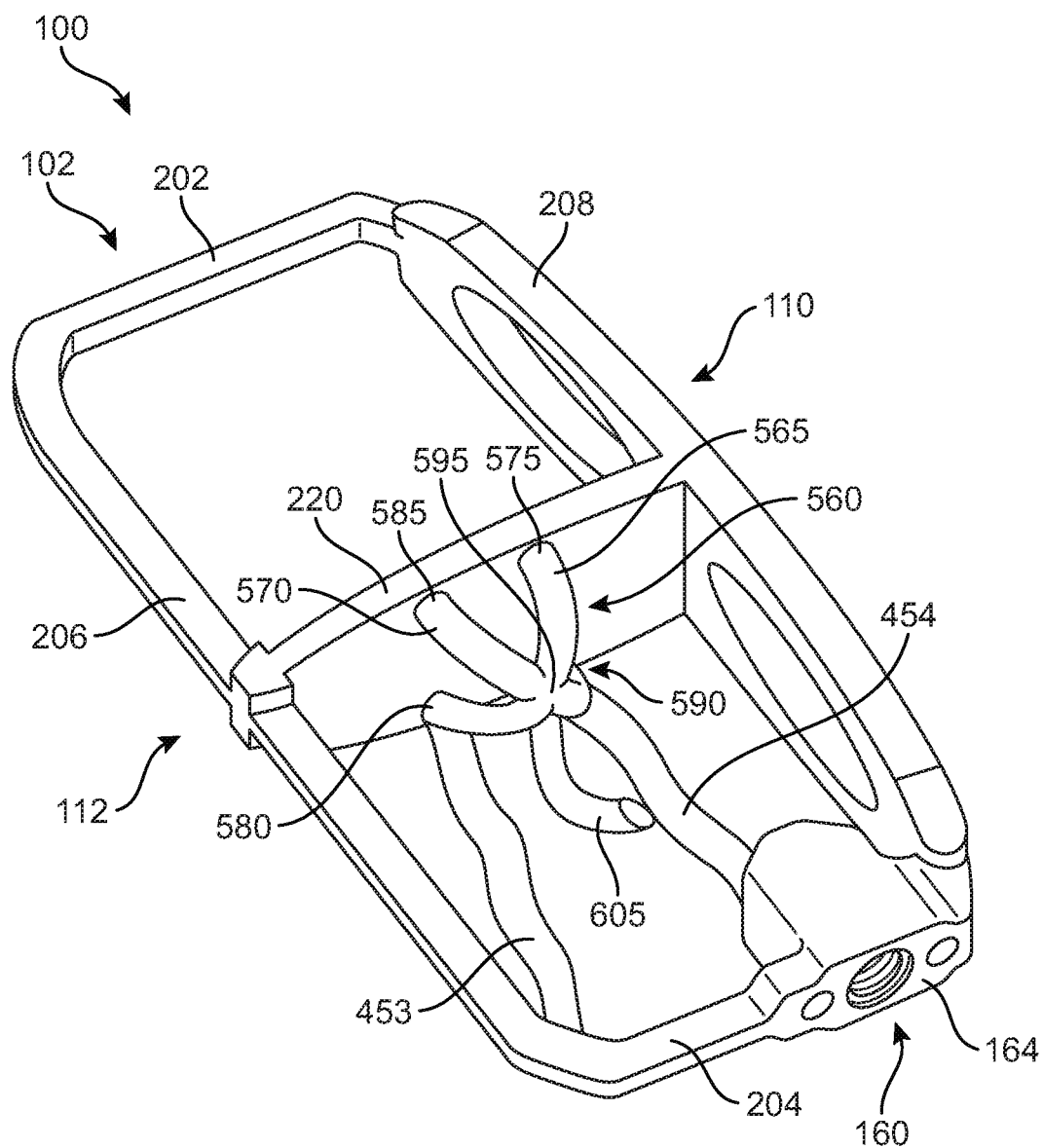
FIG. 15 is a schematic perspective lateral view of an implant as shown in FIG. 14, with a non-helical bone contacting member added in an inferior half of the implant.

FIG. 15 is a schematic perspective lateral view of an implant as shown in FIG. 14, with a non-helical bone contacting member added in an inferior half of the implant. For example, as shown in FIG. 15, a non-helical bone contacting member 605 may attach to support member 565 and support member 570 at support member junction 595. Thus, non-helical bone contacting member 605 may extend from a portion of the first support member that is disposed internal to the helical bone contacting members. Non-helical bone contacting member 605 may extend in an inferior direction to form a portion of an (inferior) exterior surface of implant 100 between helical bone contacting member 454 and helical bone contacting member 453.

Figure 16:
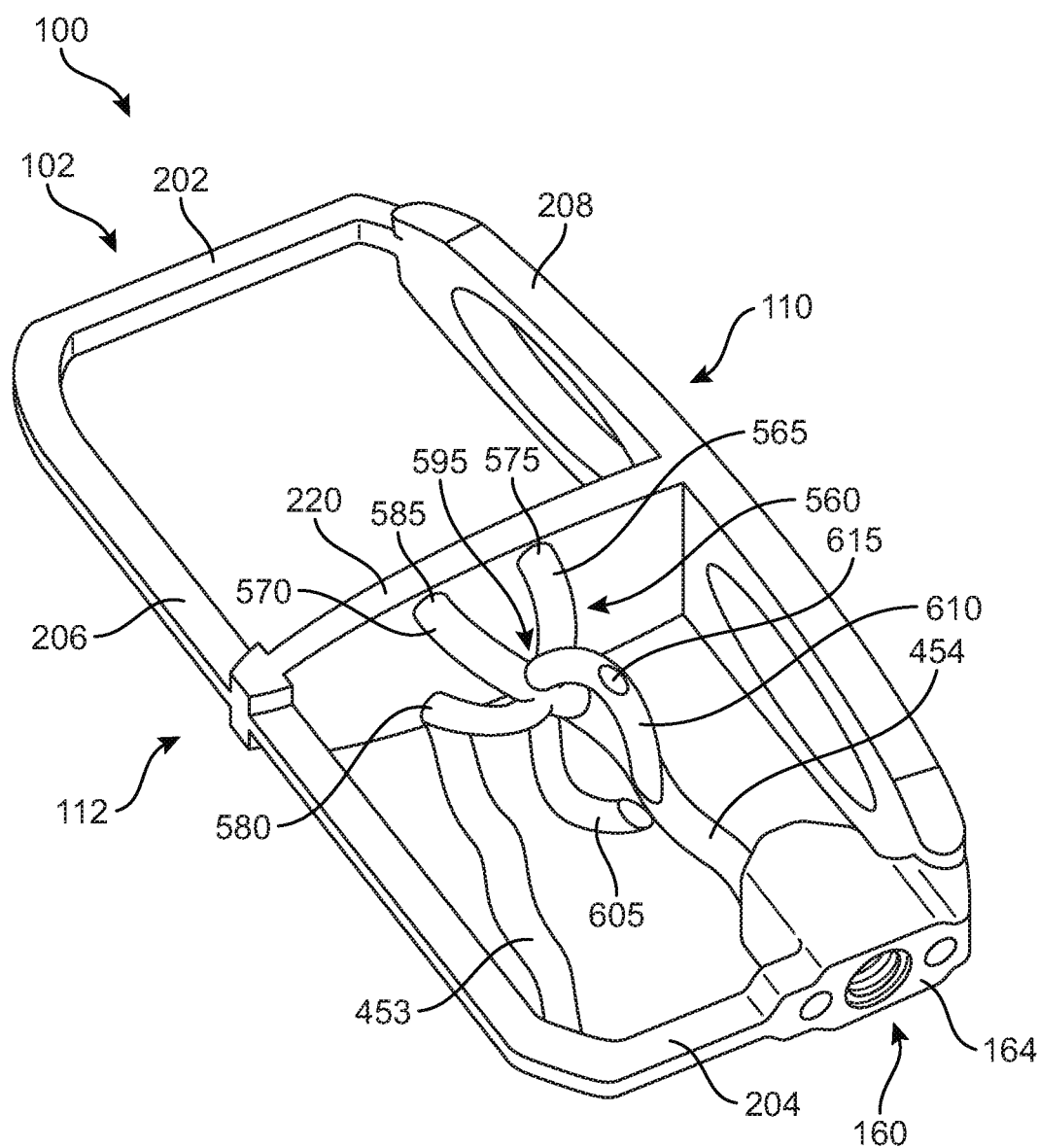
FIG. 16 is a schematic perspective lateral view of an implant as shown in FIG. 15, with a non-helical bone contacting member added in a superior half of the implant.

FIG. 16 is a schematic perspective lateral view of an implant as shown in FIG. 15, with a non-helical bone contacting member added in a superior half of the implant. As shown in FIG. 16, implant 100 may include another non-helical bone contacting member 610. Non-helical bone contacting member 610 may extend from junction 595 between support member 565 and support member 570 in a superior direction. As further shown in FIG. 16, non-helical bone contacting member 610 may include a flattened surface 615, which may form a portion of the (superior) exterior surface of implant 100.

Figure 17:
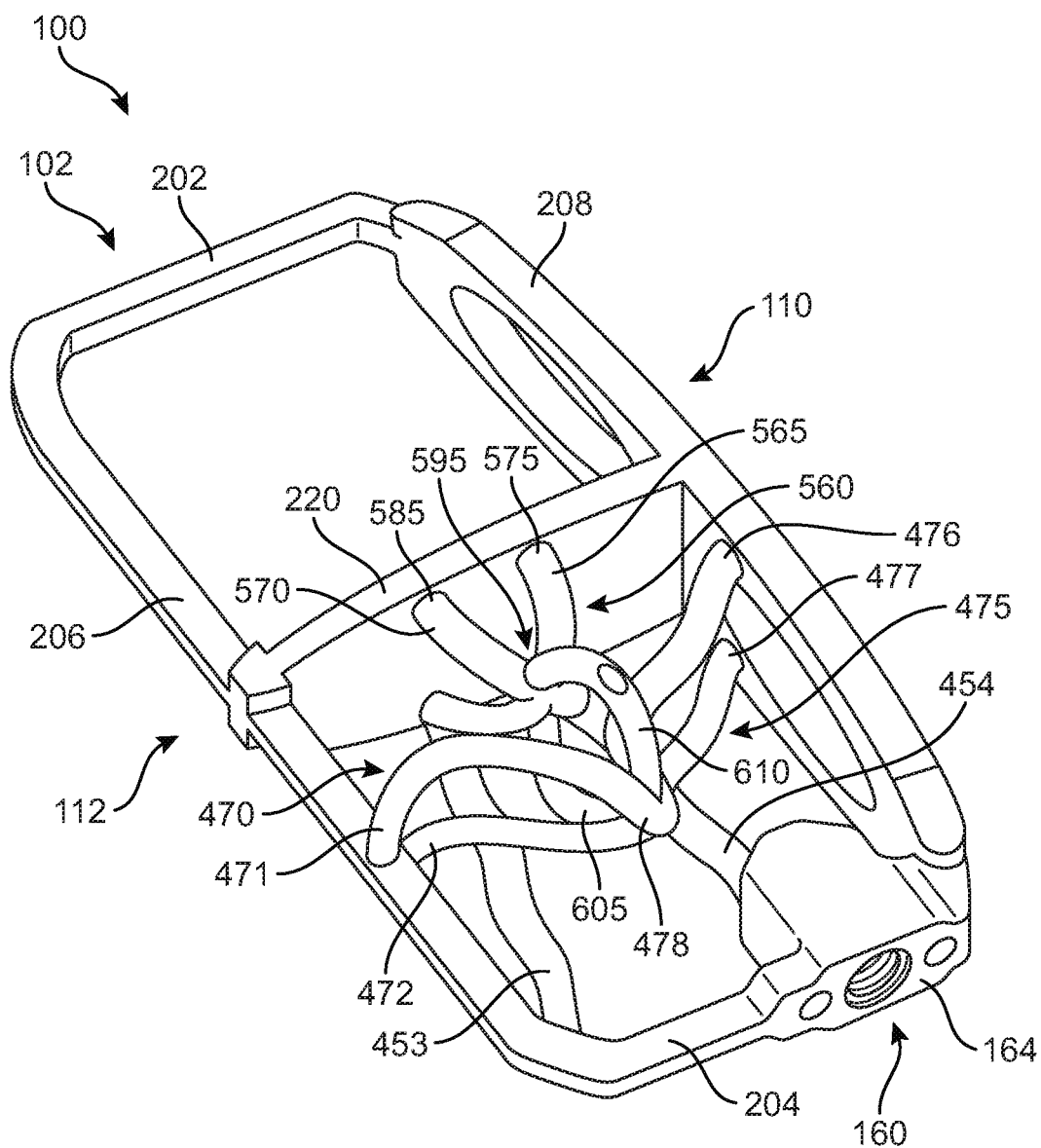
FIG. 17 is a schematic perspective lateral view of an implant as shown in FIG. 16, with two substantially U-shaped support members added.

FIG. 17 is a schematic perspective lateral view of an implant as shown in FIG. 16, with two substantially U-shaped support members added. As shown in FIG. 17, U-shaped support member 470, including first leg 471 and second leg 472 may join with U-shaped support member 475, including first leg 476 and second leg 477 at junction 478. As further shown in FIG. 17, superior non-helical bone contacting member 610 may extend from a first end at junction 595 between support member 565 and support member 570 and attach, at a second end, to U-shaped support member 470 and U-shaped support member 475 at junction 478. As further shown in FIG. 17, inferior non-helical bone contacting member 605 may extend from a first end at junction 595 between support member 565 and support member 570 and attach, at a second end, to U-shaped support member 470 and U-shaped support member 475 at junction 478.

Figure 18:
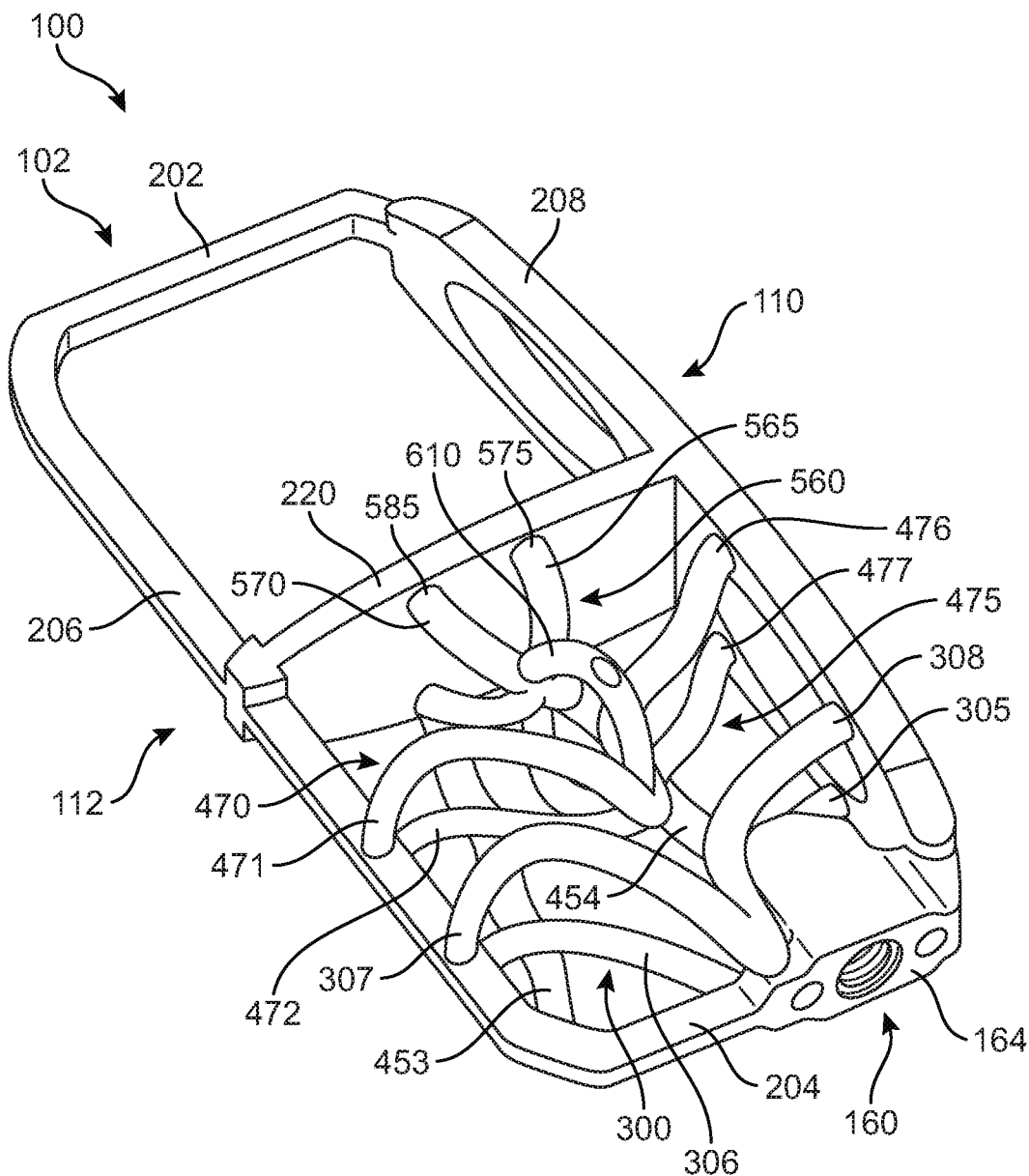
FIG. 18 is a schematic perspective lateral view of an implant as shown in FIG. 17, with a plurality of corner braces added.

FIG. 18 is a schematic perspective lateral view of an implant as shown in FIG. 17, with a plurality of corner braces added. As shown in FIG. 18, implant 100 may include fifth corner brace 305, sixth corner brace 306, seventh corner brace 307, and eighth corner brace 308. U-shaped support member 470 and U-shaped support member 475 together may form a first support structure. In addition, X-shaped member 560 may form a second support structure. As shown in FIG. 18, the first support structure and the second support structure may be generally concentric. Further, corner braces 305, 306, 307, and 308 may form a third support structure, which may be concentric with the first support structure and/or the second support structure.

Figure 19:
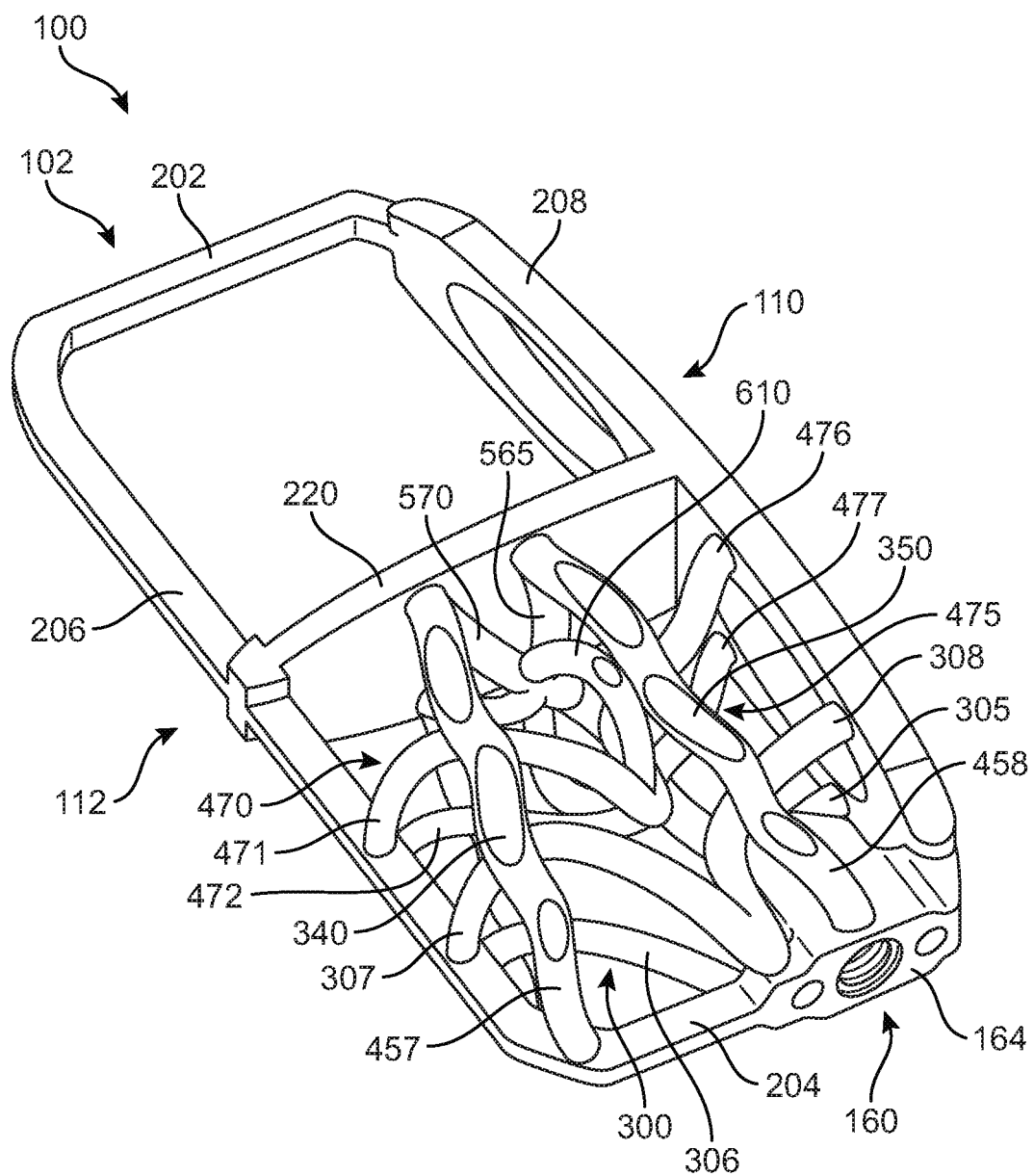
FIG. 19 is a schematic perspective lateral view of an implant as shown in FIG. 18, with helical bone contacting members added in the superior half of the implant.

FIG. 19 is a schematic perspective lateral view of an implant as shown in FIG. 18, with helical bone contacting members added in the superior half of the implant. In FIG. 19, implant 100 is shown with helical bone contacting member 457 and helical bone contacting member 458 added. Accordingly, the right half of implant 100 is shown fully assembled in FIG. 19, showing the bone contacting members, support members, and corner braces discussed above.

Figure 20:
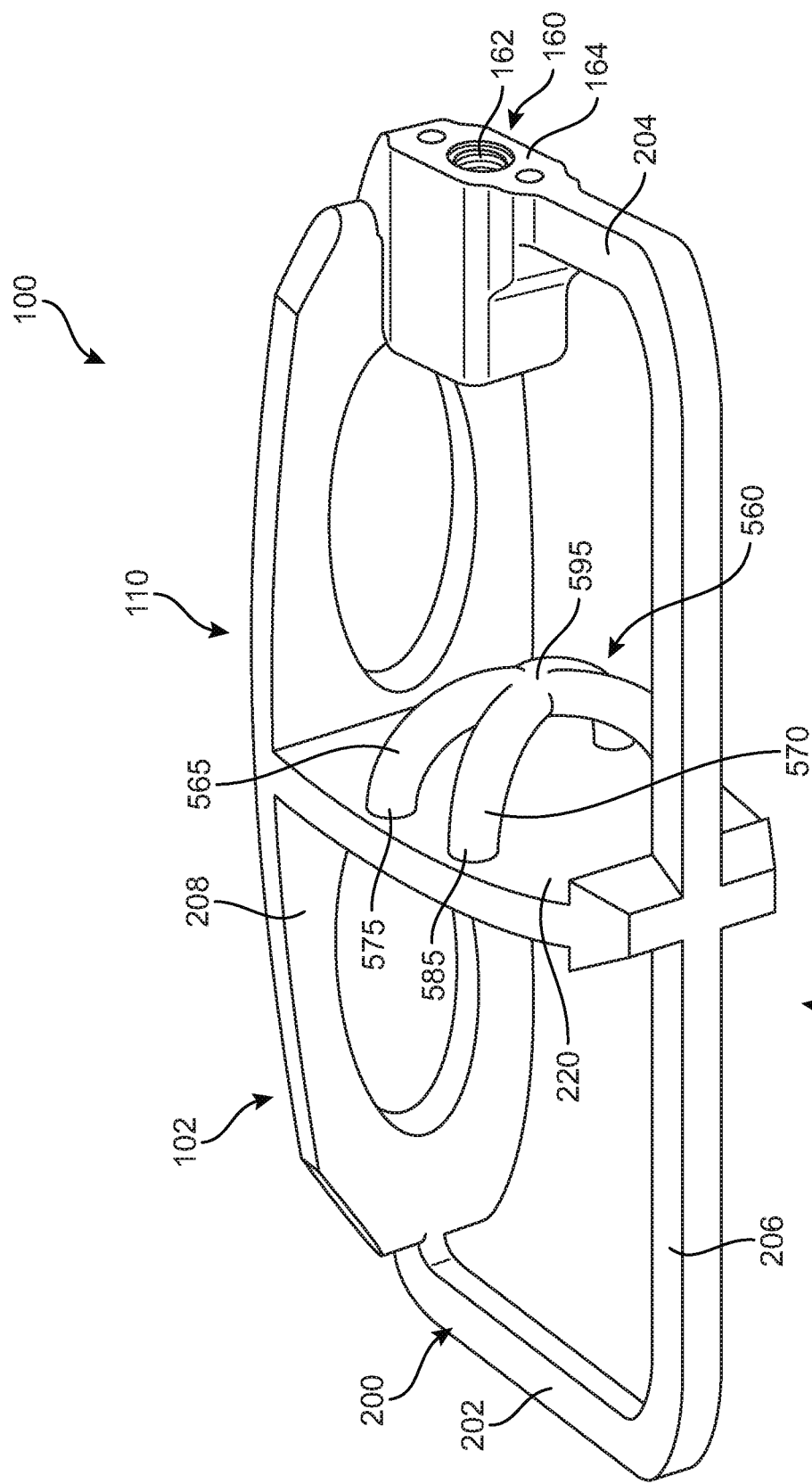
FIG. 20 is a schematic perspective posterior view of an implant with structural members removed and revealing support members in an X-shaped arrangement.

FIG. 20 is a schematic perspective posterior view of an implant with structural members removed and revealing support members in an X-shaped arrangement. That is, FIG. 20 illustrates the same select components of implant 100 as shown in FIG. 13, but at a slightly different angle to further illustrate the structure of X-shaped member 560. As shown in FIG. 20, X-shaped member 560 extends out from central wall 220 in a generally dome-shaped configuration with junction 595 forming the peak of the dome.

Figure 21:
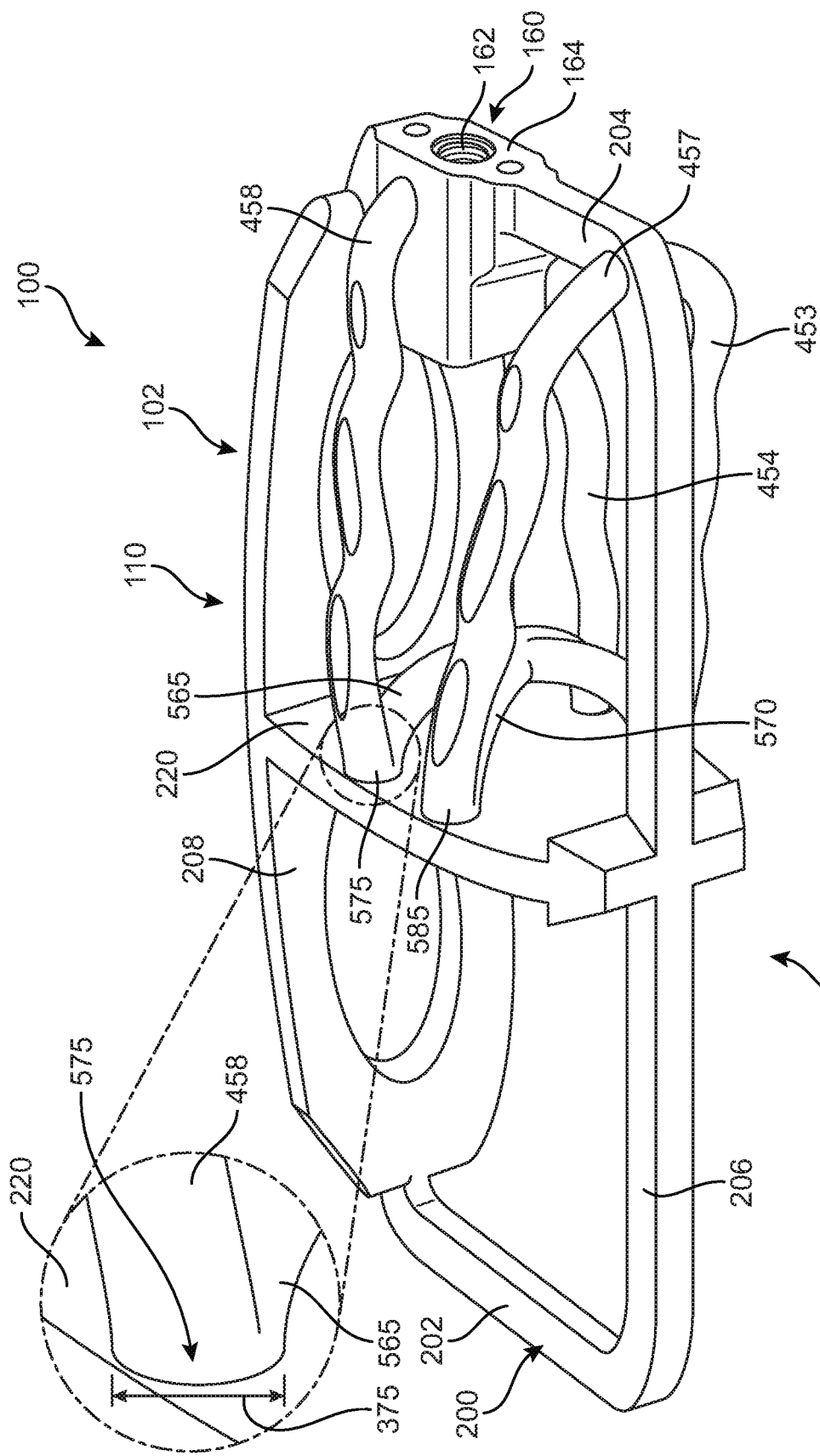
FIG. 21 is a schematic perspective posterior view of an implant as shown in FIG. 20, with a plurality of helical bone contacting members added.

FIG. 21 is a schematic perspective posterior view of an implant as shown in FIG. 20, with a plurality of helical bone contacting members added. FIG. 21 shows third helical bone contacting member 453, fourth bone contacting member 454, seventh bone contacting member 457, and eighth bone contacting member 458. As shown in FIG. 21, the plurality of third helical bone contacting member 453, fourth bone contacting member 454, seventh bone contacting member 457, and eighth bone contacting member 458 may extend from a first side of central wall 220 to the peripheral frame portion 200 and may define outer surfaces of implant 100. Bone contacting member 453 may be an inferior posterior helical bone contacting member 453 defining outer surfaces of the implant in the inferior half of the implant and toward the posterior side of the implant. In addition, bone contacting member 454 may be an inferior anterior helical bone contacting member defining outer surfaces of the implant in the inferior half of the implant and toward the anterior side of the implant. Bone contacting member 457 may be a superior posterior helical bone contacting member defining outer surfaces of the implant in the superior half of the implant and toward the posterior side of the implant. Also, bone contacting member 458 may be a superior anterior helical bone contacting member defining outer surfaces of the implant in the superior half of the implant and toward the anterior side of the implant.

As shown in FIG. 21, support member 565 may be fixedly attached to central wall 220 at junction 575 coincident with helical bone contacting member 458. As further shown in FIG. 21, support member 565 and helical bone contacting member 458 may have substantially the same size 375 and shape, and may be substantially aligned with one another at junction 575. As also shown in FIG. 21, support member 570 may be attached to body 102 at central wall 220 at junction 585 coincident with helical bone contacting member 453. Thus, support member 565 may extend from junction 575 between central wall 220 and the superior anterior helical bone contacting member 458 to a junction between central wall 220 and the inferior posterior helical bone contacting member 453. Also, support member 570 may extend from junction 585 between central wall 220 and the superior posterior helical bone contacting member 457 through a central region of the implant to a junction between central wall 220 and the inferior anterior helical bone contacting member 454.

Figure 22:
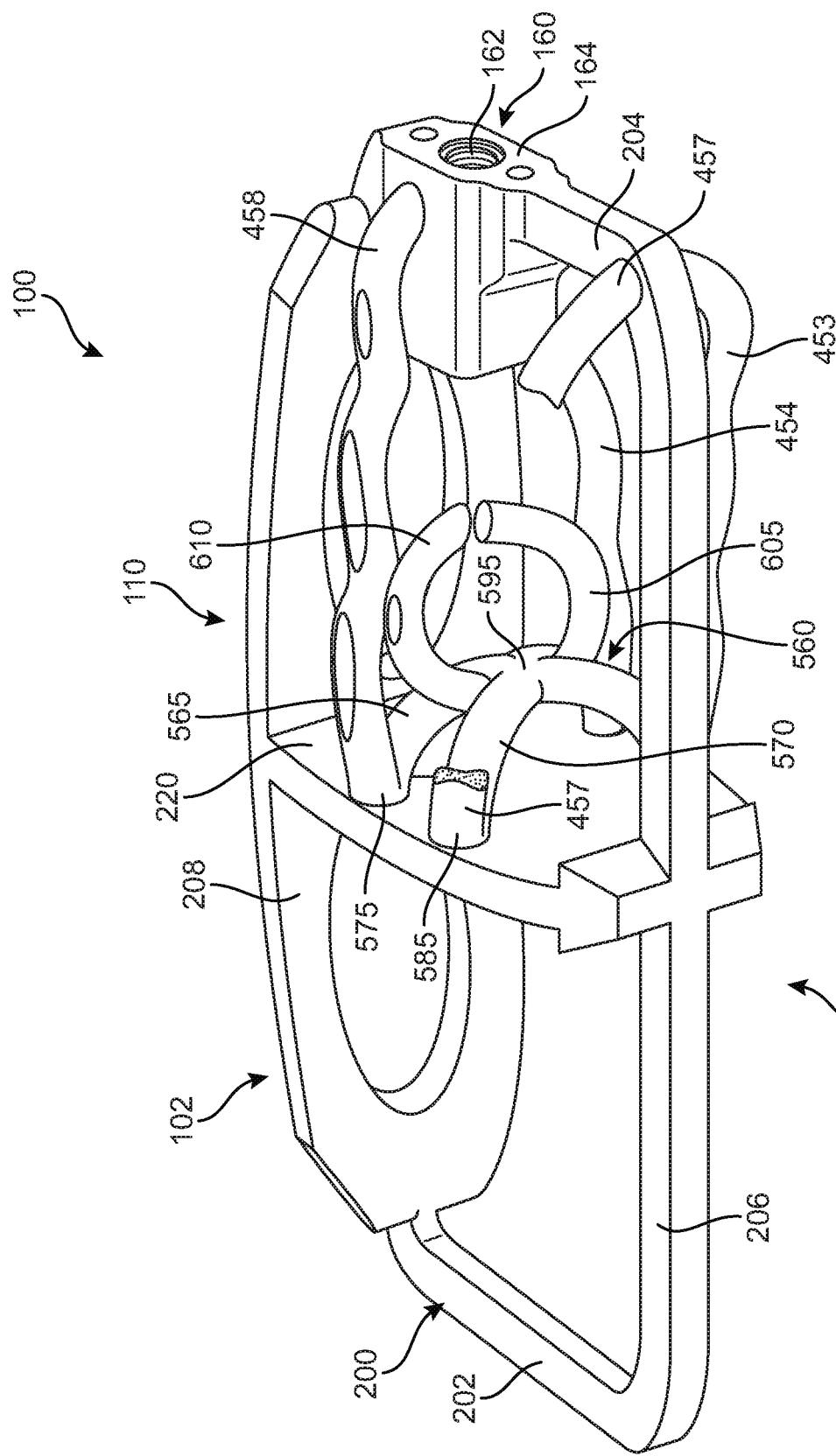
FIG. 22 is a schematic perspective posterior view of an implant as shown in FIG. 21 with one of the helical bone contacting members cutaway and with non-helical bone contacting members exposed.

FIG. 22 is a schematic perspective posterior view of an implant as shown in FIG. 21 with one of the helical bone contacting members cut away and with non-helical bone contacting members exposed. As shown in FIG. 22, the middle portion of helical bone contacting member 457 has been cutaway in order to show the support members in the interior region of implant 100.

FIG. 22 shows inferior non-helical bone contacting member 605 and superior non-helical bone contacting member 610 extending from a portion of the support member 565 and a portion of support member 570 that are disposed internal to the helical bone contacting members. As shown in FIG. 22, inferior non-helical bone contacting member 605 and superior non-helical bone contacting member 610 may extend from junction 595 where support member 565 and support member 570 intersect.

Figure 23:
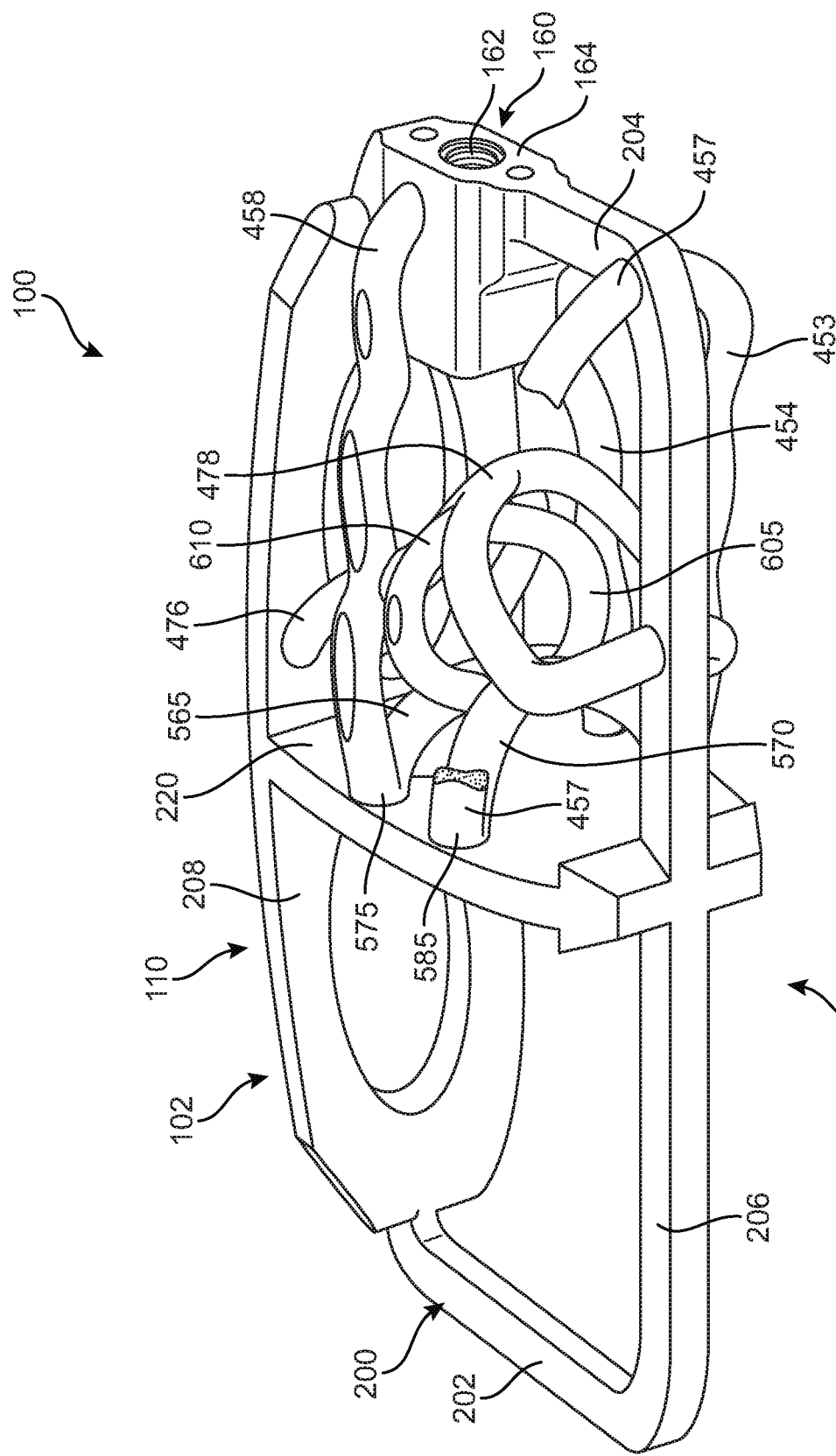
FIG. 23 is a schematic perspective posterior view of an implant as shown in FIG. 22, with two substantially U-shaped support members added.

FIG. 23 is a schematic perspective posterior view of an implant as shown in FIG. 22, with two substantially U-shaped support members added. FIG. 23 shows the addition of U-shaped support member 470 and U-shaped support member 475 attached at junction 478. As shown in FIG. 23, inferior non-helical bone contacting member 605 and superior non-helical bone contacting member 610 may attach to U-shaped support member 470 and U-shaped support member 475 at junction 478.

While FIGS. 13-23 illustrate structural members only in one half of implant 100, it will be understood that the other half of the implant (i.e., the other side of central wall 220) may include the same or substantially the same structural members. In some embodiments, the structural members on opposing sides of central wall 220 may be substantial mirror images of one another.

Open Inner Volume of Implant

The arrangement of structural members with the body may also be designed to achieve a desired total open volume. As used herein a total volume is the combined volume of any openings between structural members, any openings in the body, or between structural members and the body. This open configuration may facilitate bone growth in and through the implant. A portion, or substantially all of, the open spaces is optionally filled with a bone graft or material prior to or after insertion of the implant to facilitate bone growth.

The total volume of the open spaces (also referred to simply as the open space volume) within any particular implant is dependent on the overall dimension of the implant as well as the size and dimension of individual components within the implant including structural members, frame portions, etc. The open space volume may range from about 20% to 80% of the volume of the implant. In some embodiments, implant 100 may have an open space volume that is between 25% and 80% of the implant's total volume. In still further embodiments, implant 100 may have an open space volume that is between 40% and 75% of the total implant volume.

Due to reinforcements made to various portions of the implant, other portions of the implant may be made less robust. For example, with more support members in the inner portion of the implant, the central wall may be made thinner. Conversely, if the central wall is made thicker, fewer and/or smaller diameter support members may be used in the interior of the implant.

Non-Planar Arrangement of Structural Members

The arrangement of the structural members is generally non-planar. First, the helical nature of bone contacting members is non-planar. Second, the structural members may overlap one another instead of intersecting with one another in the same plane. Third, the outer surfaces of the implant, although substantially flush with one another, may form an outer periphery of the implant that is non-planar, as the outer shape of the implant is generally curved in at least one of the lateral direction and the anterior-posterior direction.

Figure 24:
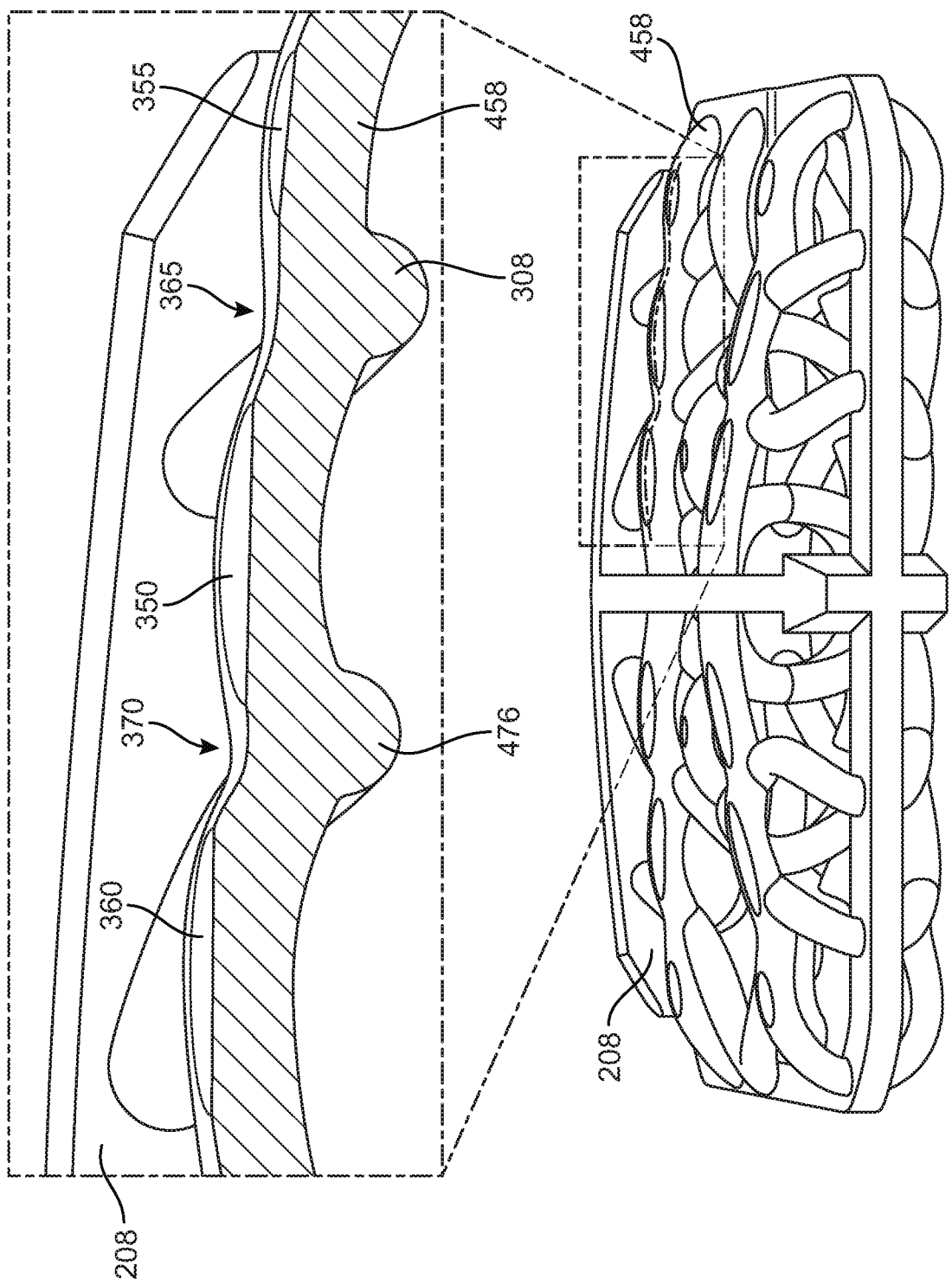
FIG. 24 is a schematic perspective posterior superior view of the implant of FIG. 1, including an enlarged cut-away view of a structural member.

In some embodiments, bone contacting members may be disposed distal to support members and/or corner braces with bone contacting members generally disposed further outwards along the superior and inferior sides of an implant than support members and/or corner braces. Thus, bone contacting members may generally be disposed closer to the vertebral end plates following implantation into the spine. As illustrated in FIG. 24, bone contacting member 458 overlaps, and is thus distal to, support member 476 and corner brace 308 on outer facing sides of support member 476 and corner brace 308.

As also shown in FIG. 24, in some embodiments, the bone contacting members may include substantially flattened surfaces to facilitate insertion and bone growth. For example, as shown FIG. 24, bone contacting member 458 may include one or more flattened surfaces, 350, 355, and 360. These flattened surfaces may be provided by removing peaks of the helical coils.

FIG. 24 illustrates an enlarged cutaway cross-sectional view of the intersection between structural members of the implant. Further, FIG. 24 shows the enlarged cutaway view of bone contacting member 458 with a backdrop of vertically oriented peripheral frame portion 208.

As shown in FIG. 24, and discussed above, bone contacting member 458 may have a substantially helical geometry. For at least this reason the helical or spiral geometry of bone contacting member 458 provides bone contacting member 458 or any combination of structural members with a non-planar geometry.

As also shown in FIG. 24, the structural members may overlap one another. For example, as illustrated in FIG. 24, bone contacting member 458 may overlap support member 476 and may also overlap corner brace 308. Thus, as shown in the enlarged view portion of FIG. 24, support member 476 and corner brace 308 extend significantly below bone contacting member 458. Accordingly, the arrangement of these structural members is non-planar for at least this additional reason.

Bone contacting member 458 may include a plurality of flattened bone contacting surfaces associated with the helical undulations of bone contacting member 458. As shown in FIG. 24, bone contacting member 458 may include first flattened surface 350, second flattened surface 355, and third flattened surface 360 associated with upward undulations of bone contacting member 458. The support members may be affixed to bone contacting member 458 between the flattened surfaces, at the downward undulations of helical bone contacting member 458. For example, as shown in FIG. 24, support member 476 may be affixed to bone contacting member 458 beneath downward undulation 370, which resides between first flattened surface 350 and third flattened surface 360. Similarly, corner brace 308 may be affixed to bone contacting member 458 beneath downward undulation 365, which resides between first flattened surface 350 and second flattened surface 355. The helical geometry of the bone contacting members as well as the overlapping arrangement of the structural members may facilitate bone growth against, and bone ingrowth within, the implant.

Figure 25:
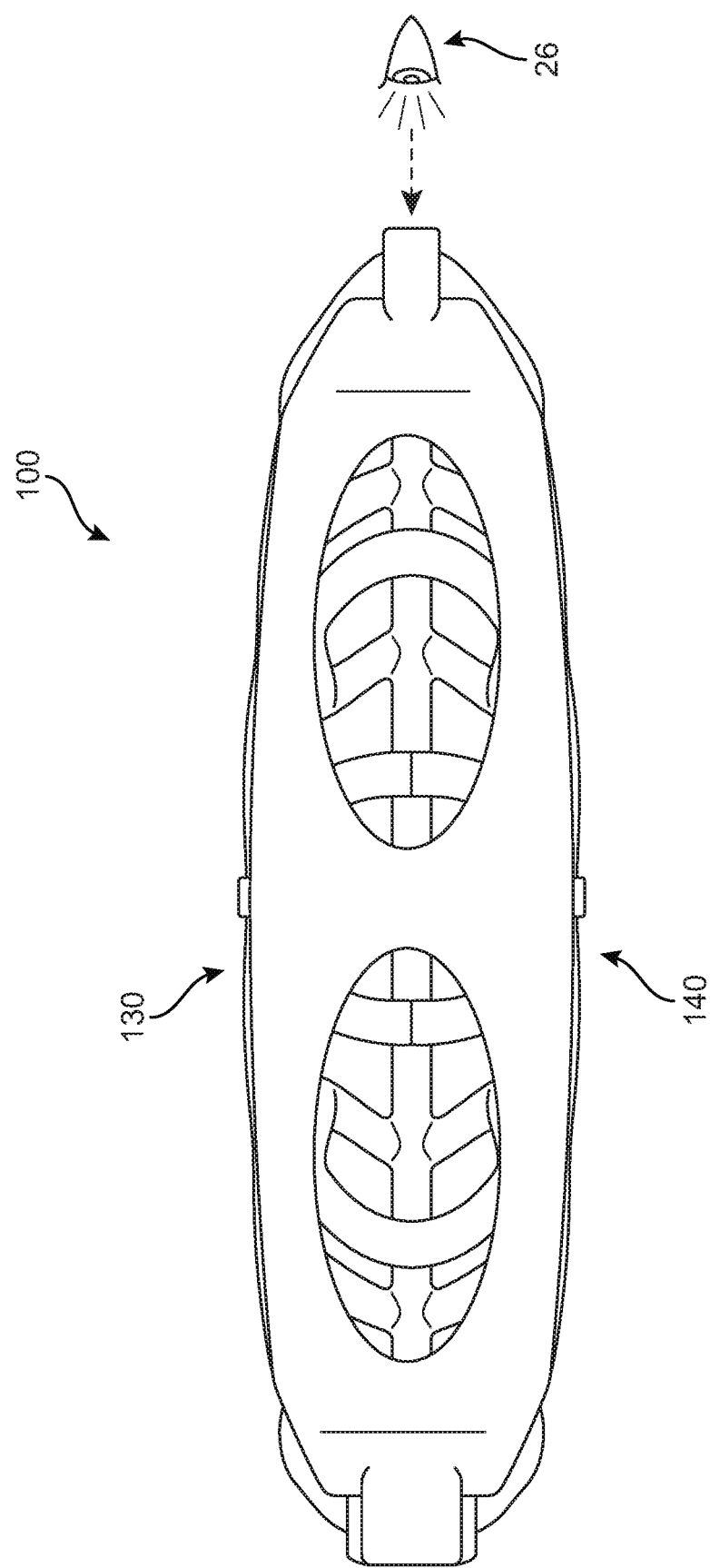
FIG. 25 is a schematic view of the implant of FIG. 1 as viewed from the anterior side.
Figure 26:
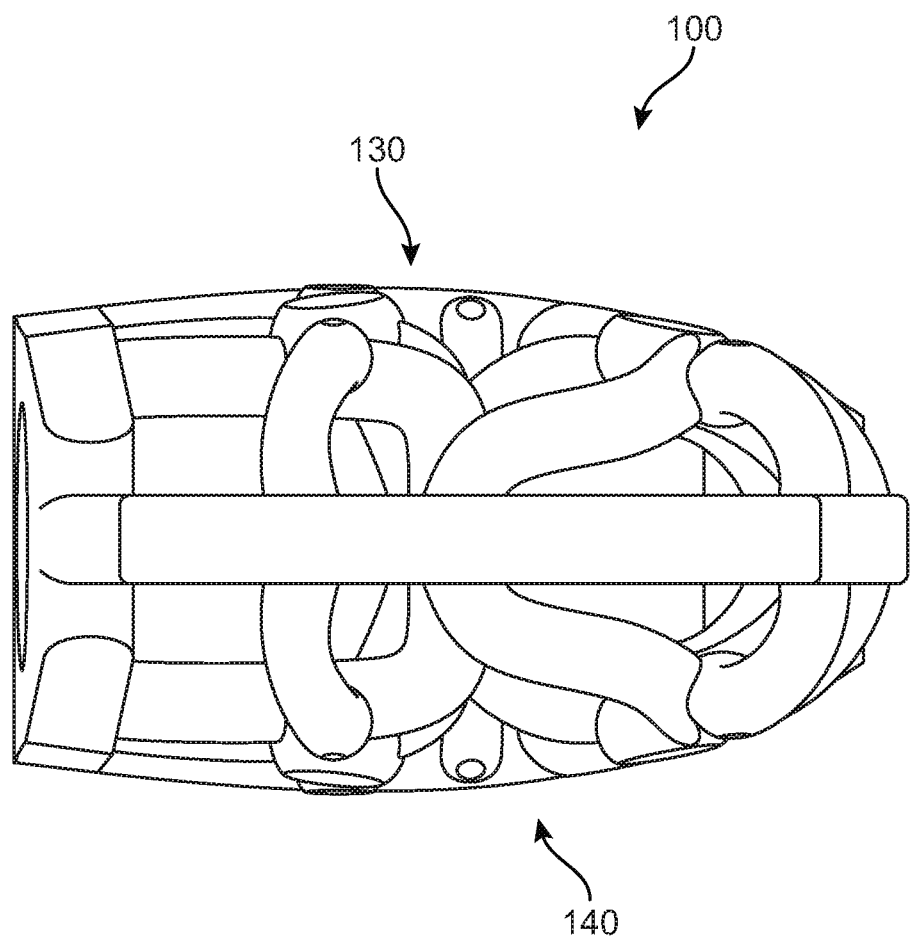
FIG. 26 is a schematic lateral view of the implant of FIG. 1 as viewed from a lateral vantage point indicated by an eye 26 in FIG. 25.

FIGS. 25 and 26 provide anterior side and lateral side (or lateral end) views, respectively, of implant 100. As seen in FIGS. 25-26, implant 100 may be configured with a bi-convex geometry. Specifically, implant 100 can be seen to have a convex superior side 130 and a similarly convex inferior side 140. Furthermore, when viewed from the lateral end shown in FIG. 26, implant 100 has an approximately convex shape along superior side 130 and the inferior side 140. Thus, it may be seen that implant 100 is convex in both the longitudinal and lateral directions, which helps to match the geometry of the vertebral endplates. Thus arranging the implant so as to have a convex outer surface on the superior and inferior sides helps to ensure that distal surfaces (i.e., "flattened surfaces") of implant 100 contact the concave surfaces of opposing vertebral plates. In other embodiments, however, the inferior and/or superior surfaces of an implant could be concave, flat, tapered/angulated to provide lordosis or kyphosis, etc. in shape.

In some embodiments, at least one lateral side of an implant may be shaped to facilitate easy insertion. As best seen in FIGS. 25-26, by virtue of the tapered geometry of implant 100, the lateral side of implant 100 is configured as a rounded end to improve ease of insertion. In some cases, this may be referred to as a "bulleted nose" configuration.

Embodiments can also be provided with various flat/parallel (0-degree), lordotic, and hyper-lordotic angles. In some embodiments, the implant can be configured with an approximately 8-degree angle between the superior and inferior surfaces. In other embodiments, the implant can be configured with an approximately 15-degree angle between the superior and inferior surfaces. In still other embodiments, the implant can be configured with an approximately 20-degree angle between the superior and inferior surfaces. Still other angles are possibly including any angles in the range between 0 and 30 degrees. Still other embodiments can provide a lordotic angle of less than 8 degrees. Still other embodiments can provide a hyper-lordotic angle of more than 20 degrees. In at least some embodiments, the lordotic angle of the implant is accomplished via the geometry of the central keel portion and the side frame portion (posterior or anterior).

Figure 27:
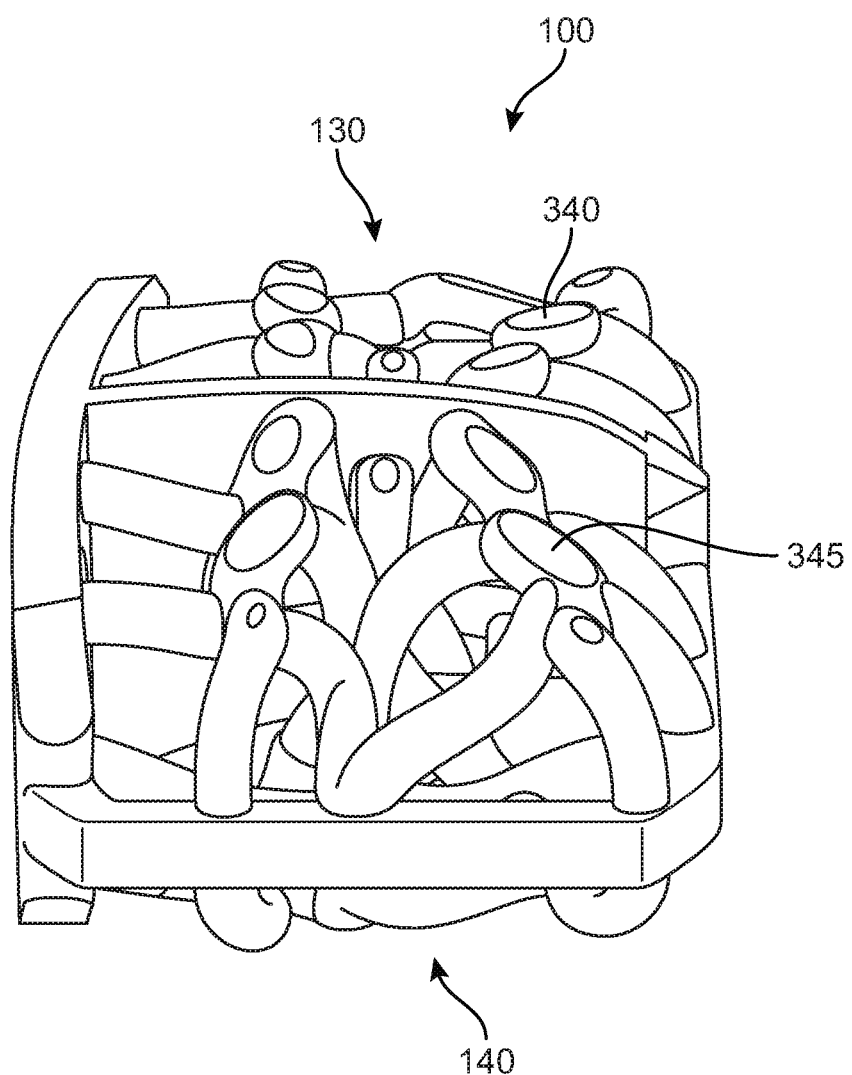
FIG. 27 is a schematic perspective lateral view of the implant of FIG. 1.

FIG. 27 is a schematic perspective lateral view of the implant of FIG. 1. FIG. 27 further illustrates the bi-convex geometry of implant 100 discussed above. In addition, FIG. 27 also illustrates that the flattened surfaces (e.g., flattened surfaces 340 and 345) of the structural members are generally flush with one another and form the outer surfaces of the implant in one or more sections of the implant. As shown in FIG. 27, these flattened surfaces may be flush with one another along a generally curved (i.e., non-planar) surface. This may facilitate implantation as well as bone growth as discussed above.

Implantation

Figure 28:
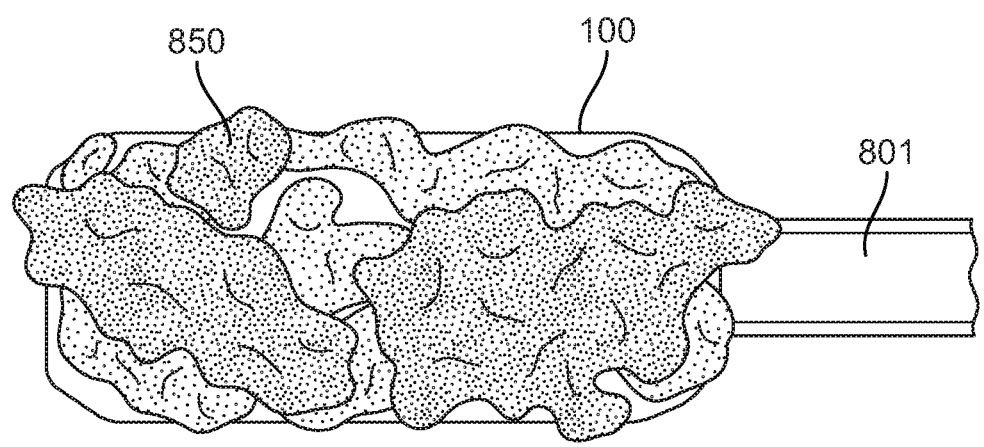
FIG. 28 is a schematic view depicting an implant attached to an implant tool, and where the implant is covered with a bone growth promoting material, according to an embodiment.
Figure 29:
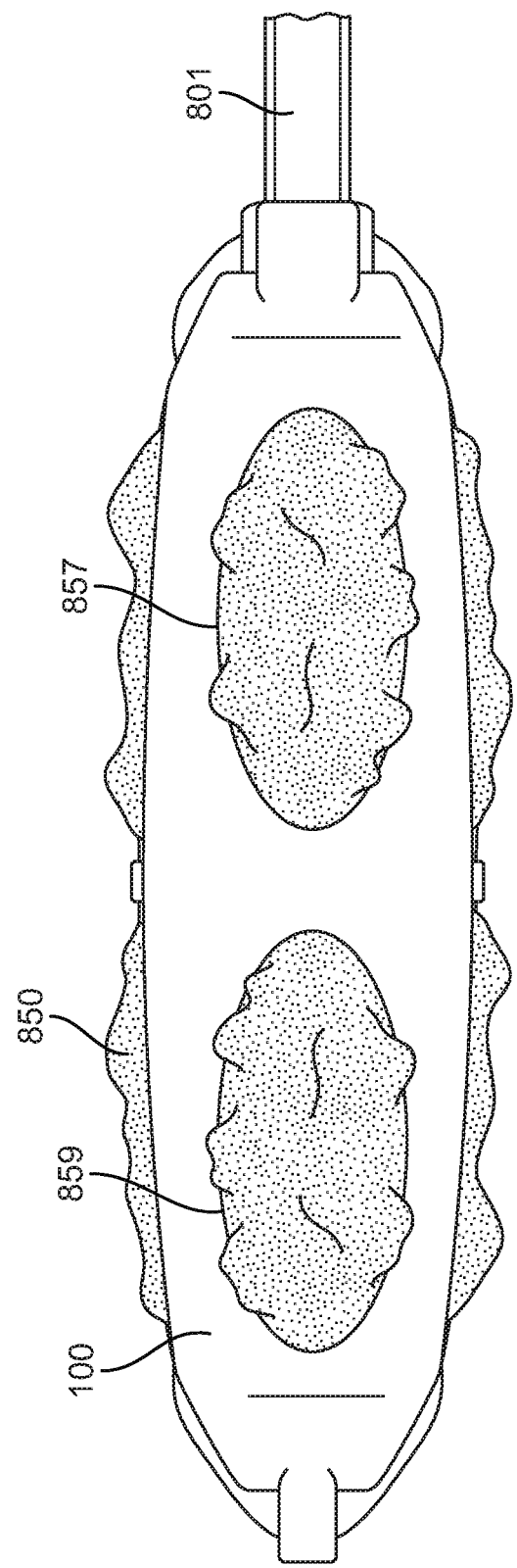
FIG. 29 is a schematic anterior view of an implant filled with bone growth promoting material.

FIGS. 28-31 illustrate various schematic views of a process of implanting an implant 800. Referring first to FIGS. 28-29, the implantation process may begin with the application of a bone growth promoting material, also referred to as a BGPM, to the implant. As used herein, a "bone growth promoting material" is any material that helps bone growth. Bone growth promoting materials may include provisions that are freeze dried onto a surface or adhered to the metal through the use of linker molecules or a binder. Examples of bone growth promoting materials are any materials including bone morphogenetic proteins (BMPs), such as BMP-1, BMP-2, BMP-4, BMP-6, and BMP-7. These are hormones that convert stem cells into bone forming cells. Further examples include recombinant human BMPs (rhBMPs), such as rhBMP-2, rhBMP-4, and rhBMP-7. Still further examples include platelet derived growth factor (PDGF), fibroblast growth factor (FGF), collagen, BMP mimetic peptides, as well as RGD peptides. Generally, combinations of these chemicals may also be used. These chemicals can be applied using a sponge, matrix or gel.

Some bone growth promoting materials may also be applied to an implantable prosthesis through the use of a plasma spray or electrochemical techniques. Examples of these materials include, but are not limited to, hydroxyapatite, beta tri-calcium phosphate, calcium sulfate, calcium carbonate, as well as other chemicals.

A bone growth promoting material can include, or may be used in combination with a bone graft or a bone graft substitute. A variety of materials may serve as bone grafts or bone graft substitutes, including autografts (harvested from the iliac crest of the patient's body), allografts, demineralized bone matrix, and various synthetic materials.

Some embodiments may use autograft. Autograft provides the spinal fusion with calcium collagen scaffolding for the new bone to grow on (osteoconduction). Additionally, autograft contains bone-growing cells, mesenchymal stem cells and osteoblast that regenerate bone. Lastly, autograft contains bone-growing proteins, including bone morphogenic proteins (BMPs), to foster new bone growth in the patient.

Bone graft substitutes may comprise synthetic materials including calcium phosphates or hydroxyapatites, stem cell containing products which combine stem cells with one of the other classes of bone graft substitutes, and growth factor containing matrices such as INFUSE® (rhBMP-2-containing bone graft) from Medtronic, Inc.

It should be understood that the provisions listed here are not meant to be an exhaustive list of possible bone growth promoting materials, bone grafts or bone graft substitutes.

In some embodiments, BGPM may be applied to one or more outer surfaces of an implant. In other embodiments, BGPM may be applied to internal volumes within an implant. In still other embodiments, BGPM may be applied to both external surfaces and internally within an implant. As seen in FIGS. 28-29, a BGPM 850 has been placed inside an interior of implant 800 and also applied on superior and inferior surfaces of implant 800. Moreover, as shown in FIG. 29, BGPM 850 has been inserted through (and extends through) a first window 857 and a second window 859 of implant 800.

As shown in FIG. 29, a method of inserting implant 100 may include filling the inner volume of implant 100 with bone growth promoting material around the support members.

Figure 30:
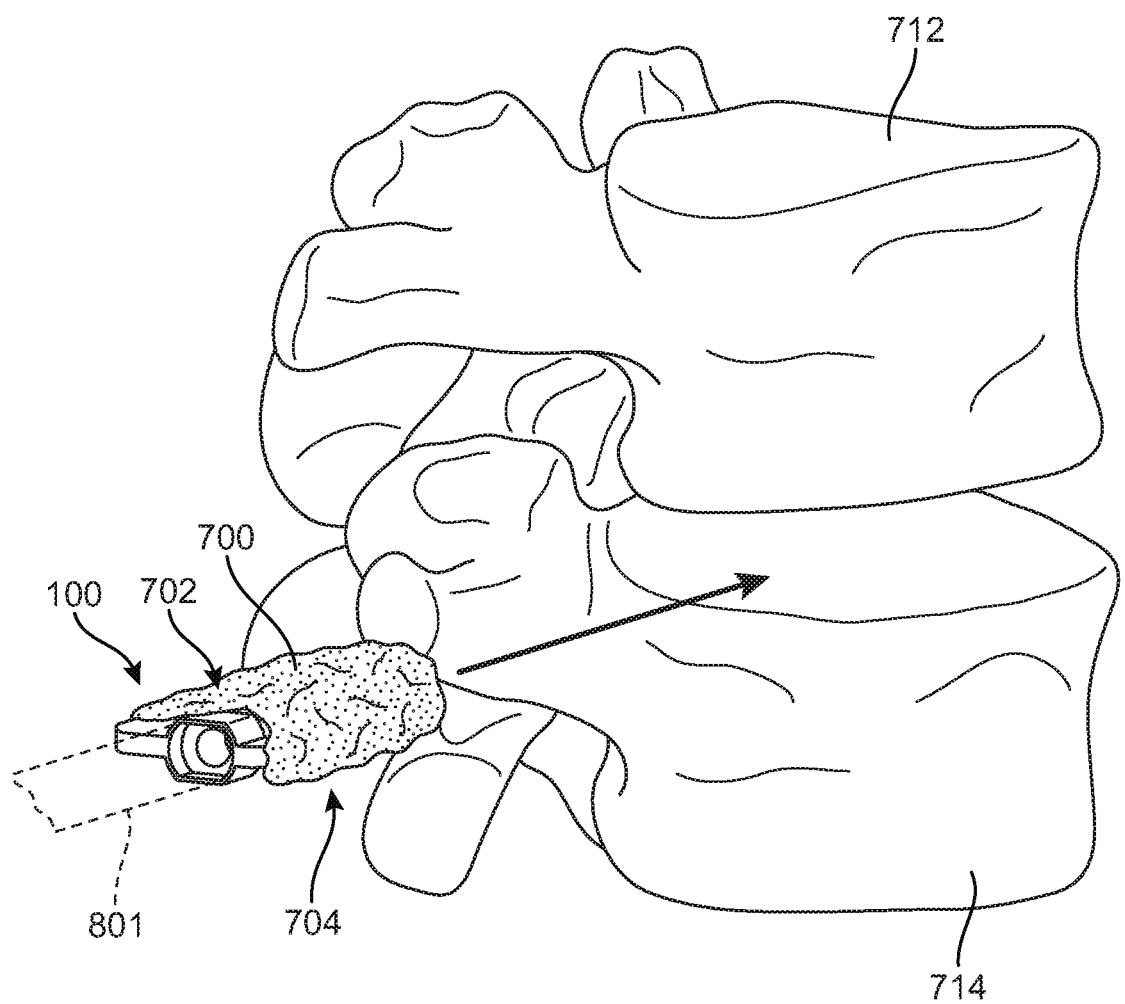
FIG. 30 is a schematic perspective view of an implant being positioned for insertion between two vertebrae, according to an embodiment.
Figure 31:
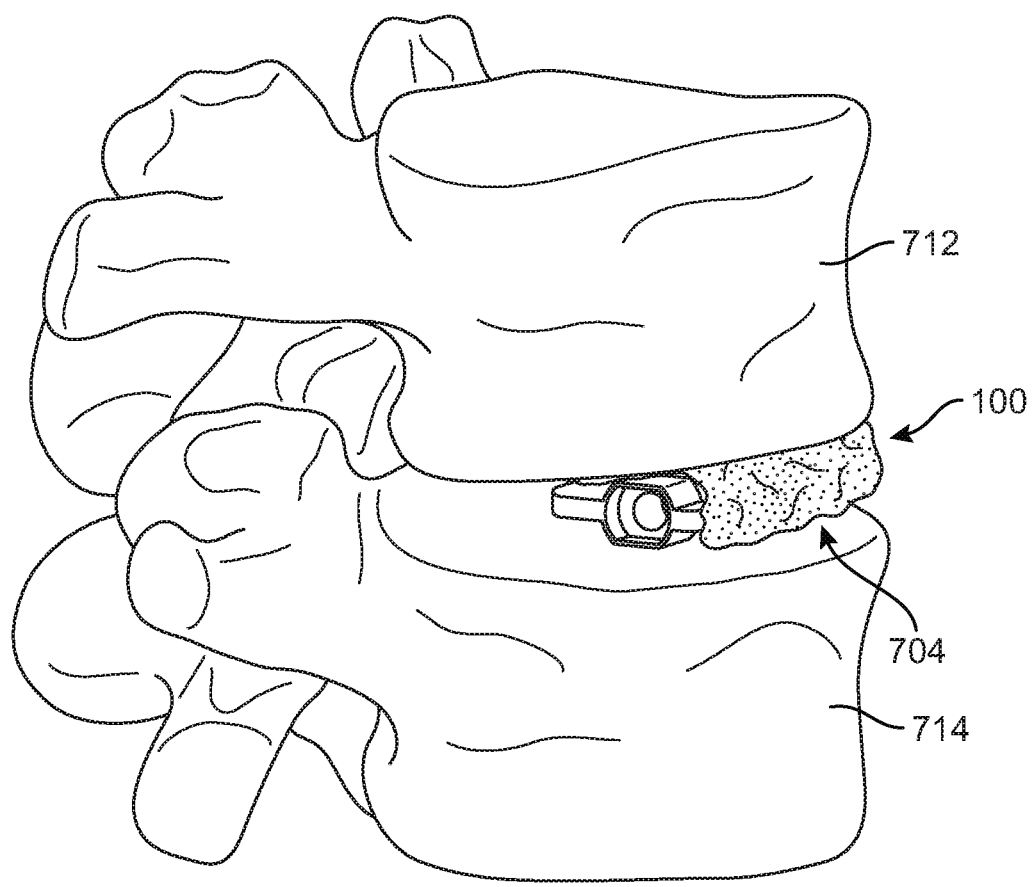
FIG. 31 is a schematic isometric view of the implant of FIG. 30 inserted between the two vertebrae.

FIGS. 30 and 31 show schematic views of the implant pre-implantation (FIG. 30) and post-implantation (FIG. 31). Once implanted, implant 800 may be disposed between, and in direct contact with, adjacent vertebra. Specifically, a superior side 702 of implant 700 is disposed against first vertebra 712. Likewise, an inferior side 704 of implant 700 is disposed against second vertebra 714.

In different embodiments, implantation methods could vary. In some embodiments, implant 800 may be secured to an implantation tool 701 (partially seen in FIGS. 28-29) that is used to drive implant 800 into the spine. Implantation tool 701 could be any rod, ram, pole or other device that can be hammered, rammed, or otherwise driven to position implant 800 between adjacent vertebrae. As previously mentioned, in some cases, an implantation tool could be attached to implant 800 at a fastener receiving portion (i.e., a threaded opening for receiving a threaded shaft from a tool).

The implants for use in the spine have overall dimensions suitable for insertion in the spine, typically between two vertebral bodies. The shape of the implant and dimensions depends on the site into which it is inserted. Exemplary heights for implants such as implant 100 and implant 700 include, but are not limited to, 5 mm to 30 mm. Other embodiments could have incremental heights of any value in the range between the aforementioned range, most often between 8 mm and 16 mm. Still other embodiments could have a height greater than 16 mm. Still other embodiments could have a height less than 8 mm. Additionally, the horizontal footprint of the implant could vary. Exemplary footprint sizes for any embodiments of the implant include, but are not limited to, 15-20 mm in the anterior-posterior direction and 40-60 mm in the lateral-lateral direction. Still other embodiments could be configured with any other footprint sizes.

The dimensions of one or more structural members could vary. In some embodiments, a structural member could have a cross-sectional diameter in a range between 0.2 and 3 mm. For structural members with polygonal cross sections, the dimensions characterizing the polygon (e.g., first and second diameters for an ellipse) could vary. As an example, a structural member with an elliptic cross section could have a cross section with a first diameter in a range between 0.2 mm and 3 mm and a second diameter in range between 0.2 mm and 3 mm. In other embodiments, a structural member could have any other cross-sectional diameter. Moreover, in some cases a bone contacting member and a support member could have similar cross-sectional diameters while in other cases a bone contacting member and a support member could have different cross-sectional diameters.

The various components of an implant may be fabricated from biocompatible materials suitable for implantation in a human body, including but not limited to, metals (e.g. titanium or other metals), synthetic polymers, ceramics, and/or their combinations, depending on the particular application and/or preference of a medical practitioner.

Generally, the implant can be formed from any suitable biocompatible, non-degradable material with sufficient strength. Typical materials include, but are not limited to, titanium, biocompatible titanium alloys (e.g. γTitanium Aluminides, $Ti_6$—$Al_4$—V ELI (ASTM F 136 and F 3001), or $Ti_6$—$Al_4$—V (ASTM F 2989, F 1108 and ASTM F 1472)) and inert, biocompatible polymers, such as polyether ether ketone (PEEK) (e.g. PEEK-OPTIMA®, Invibio Inc and Zeniva Solvay Inc.). Optionally, the implant contains a radiopaque marker to facilitate visualization during imaging.

In different embodiments, processes for making an implant can vary. In some embodiments, the entire implant may be manufactured and assembled via readditional/CNC machining, injection-molding, casting, insert-molding, co-extrusion, pultrusion, transfer molding, overmolding, compression molding, 3-Dimensional (3-D) printing (including Direct Metal Laser Sintering and Electron Beam Melting), dip-coating, spray-coating, powder-coating, porous-coating, milling from a solid stock material and their combinations. Moreover, the embodiments can make use of any of the features, parts, assemblies, processes and/or methods disclosed in the "The Coiled Implant Application".

While various embodiments have been described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. An implant, comprising:
    a body defining a transverse plane dividing the implant into a superior half and an inferior half, the implant having an anterior side and a posterior side;
    a peripheral frame portion defining a periphery of the body;
    a central wall extending from a first side of the peripheral frame portion to a second side of the peripheral frame portion;
    a first helical bone contacting member attached to the body at the central wall and disposed within the superior half of the implant on a first side of the central wall;
    a first support member attached to the body at the central wall at a junction coincident with the first helical bone contacting member and the first support member extending to a central region of the implant in an internal region of the implant, to the first helical bone contacting member; and
    a non-helical bone contacting member extending from a portion of the first support member that is disposed in an internal region of the implant, to the first helical bone contacting member.

2. The implant of claim 1, further comprising:
    a second helical bone contacting member attached to the body and disposed within the superior half of the implant, wherein the first helical bone contacting member is disposed on a first side of the implant and the second helical bone contacting member is disposed on a second side of the implant;
    a second support member attached to the body at the central wall and extending to the central region of the implant;
    wherein the first support member and the second support member are connected to one another at a support member junction in the central region inward of the helical bone contacting members; and
    wherein the non-helical bone contacting member extends from the support member junction between the first support member and the second support member.

3. The implant of claim 2, wherein the first support member and the second support member are substantially U-shaped and are connected to one another at the bottoms of the two U-shapes in the central region of the implant inward of the bone contacting members.

4. The implant of claim 2, further including a third support member and a fourth support member extending from the central wall, the third support member and the fourth support member intersecting one another at a second support member junction to form a substantially X-shaped configuration.

5. The implant of claim 4, wherein a second non-helical bone contacting member attaches to the third support member and the fourth support member at the second support member junction.

6. The implant of claim 5, wherein:
    the first support member and the second support member together form a first support structure;
    the third support member and the fourth support member form a second support structure; and
    the first support structure and the second support structure are generally concentric.

7. The implant of claim 4, wherein the third support member attaches to the central wall at a junction coincident with the second helical bone contacting member.

8. The implant of claim 7, further including a third helical bone contacting member attached to the body at the central wall and disposed within the superior half of the implant on a second side of the central wall;

wherein the fourth support member attaches to the central wall at a junction coincident with the third helical bone contacting member.

9. The implant of claim 1, wherein the first helical bone contacting member overlaps the first support member on an outer-facing side of the first support member.

10. The implant of claim 1, wherein the first helical bone contacting member is attached to the central wall and extends to the peripheral frame portion.

11. An implant, comprising:
a body defining a transverse plane dividing the implant into a superior half and an inferior half, the implant having an anterior side and a posterior side;
a peripheral frame portion defining a periphery of the body;
a central wall extending from a first side of the peripheral frame portion to a second side of the peripheral frame portion;
a plurality of helical bone contacting members extending from a first side of the central wall to the peripheral frame portion and defining outer surfaces of the implant, the plurality of helical bone contacting members including:
  a superior anterior helical bone contacting member defining outer surfaces of the implant in the superior half of the implant and toward the anterior side of the implant;
  a superior posterior helical bone contacting member defining outer surfaces of the implant in the superior half of the implant and toward the posterior side of the implant;
  an inferior anterior helical bone contacting member defining outer surfaces of the implant in the inferior half of the implant and toward the anterior side of the implant; and
  an inferior posterior helical bone contacting member defining outer surfaces of the implant in the inferior half of the implant and toward the posterior side of the implant;
a first support member extending from a junction between the central wall and the superior anterior helical bone contacting member to a junction between the central wall and the inferior posterior helical bone contacting member; and
a second support member extending from a junction between the central wall and the superior posterior helical bone contacting member through a central region of the implant to a junction between the central wall and the inferior anterior helical bone contacting member;
wherein the first support member and the second support member intersect with one another at a first support member junction to form a substantially X-shaped member with the first support member junction disposed in the central region of the implant.

12. The implant of claim 11, further including a plurality of helical bone contacting members extending from a second side of the central wall to the peripheral frame portion and defining outer surfaces of the implant, the plurality of helical bone contacting members including:
  a second superior anterior helical bone contacting member defining outer surfaces of the implant in the superior half of the implant and toward the anterior side of the implant;
  a second superior posterior helical bone contacting member defining outer surfaces of the implant in the superior half of the implant and toward the posterior side of the implant;
  a second inferior anterior helical bone contacting member defining outer surfaces of the implant in the inferior half of the implant and toward the anterior side of the implant; and
  a second inferior posterior helical bone contacting member defining outer surfaces of the implant in the inferior half of the implant and toward the posterior side of the implant.

13. The implant of claim 11, further including:
a third support member extending from a junction between the central wall and the second superior anterior helical bone contacting member to a junction between the central wall and the second inferior posterior helical bone contacting member; and
a fourth support member extending from a junction between the central wall and the second superior posterior helical bone contacting member through the central region of the implant to a junction between the central wall and the second inferior anterior helical bone contacting member;
wherein the third support member and the fourth support member intersect with one another at a second support member junction to form a second substantially X-shaped member with the second support member junction disposed in the central region of the implant.

14. The implant of claim 11, wherein a non-helical bone contacting member attaches to the first support member and the second support member at the first support member junction.

15. An implant, comprising:
a body defining a transverse plane dividing the implant into a superior half and an inferior half, the implant having an anterior side and a posterior side;
a peripheral frame portion lying substantially in the transverse plane and defining a periphery of the body;
a first helical bone contacting member attached to the body and disposed within the superior half of the implant on the posterior side of the implant;
a second helical bone contacting member attached to the body and disposed within the superior half of the implant on the anterior side of the implant;
a first support member extending from a first point on a superior side of the peripheral frame portion to the first helical bone contacting member and further extending inwardly of the first helical bone contacting member into a central region of the implant and terminating at a second point on an inferior side of the peripheral frame portion adjacent to the first point from which the first support member extends;
a second support member extending from a third point on the peripheral frame portion opposite the first point to the second helical bone contacting member and further extending inwardly of the bone contacting members and terminating at a fourth point on the peripheral frame portion;
wherein the first point and the second point on the peripheral frame portion are disposed on the posterior side of the implant and the third point and the fourth point are disposed on the anterior side of the implant;
wherein the first support member and the second support member are substantially U-shaped and are connected to one another at the bottoms of the two U-shapes forming a support member junction in the central region of the implant inward of the bone contacting members; and a non-helical bone contacting member extending from the support member junction in a superior direction to a bone contacting surface.

16. The implant of claim 15, further including:

a central wall extending from a first side of the peripheral frame portion to a second side of the peripheral frame portion; and an X-shaped support structure fixedly attached to the central wall, the X-shaped support structure including a third support member and a fourth support member intersecting one another at a second support member junction;

wherein the non-helical bone contacting member is fixedly attached to the second support member junction.

17. The implant of claim 16, wherein the first helical bone contacting member is attached to the central wall and extends to the peripheral frame portion.

18. The implant of claim 16, wherein the third support member is fixedly attached to the central wall at a junction coincident with the first helical bone contacting member.

19. The implant of claim 16, wherein the fourth support member is fixedly attached to the central wall at a junction coincident with the second helical bone contacting member.

20. The implant of claim 16, wherein:

the first support member and the second support member together form a first support structure;

the third support member and the fourth support member form a second support structure; and the first support structure and the second support structure are generally concentric.

* * * * *